United States Patent [19]

Geesin et al.

[11] Patent Number: 5,747,010

[45] Date of Patent: May 5, 1998

[54] PHOTOPROTECTIVE LIPOPHILIC ANTIOXIDANT COMPOUNDS AND THEIR USE TO PREVENT UVA-MEDIATED LIPID PEROXIDATION

[75] Inventors: Jeffrey C. Geesin, Doylestown; Curtis A. Cole, Langhorne; Stephen J. Wisniewski, Doylestown, all of Pa.

[73] Assignee: Johnson & Johnson Consumer Products, Inc., Skillman, N.J.

[21] Appl. No.: 664,014

[22] Filed: Jun. 12, 1996

[51] Int. Cl.$^6$ .............................. A61K 7/42; A61K 7/44; A61K 7/00

[52] U.S. Cl. .............................. 424/59; 424/60; 424/400; 424/401

[58] Field of Search .............................. 424/59, 60, 400, 424/401

[56] References Cited

U.S. PATENT DOCUMENTS

| | | | |
|---|---|---|---|
| 4,847,072 | 7/1989 | Bissett et al. | 424/59 |
| 5,279,817 | 1/1994 | Franco | 424/59 |
| 5,445,815 | 8/1995 | Siegfried | 424/59 |

OTHER PUBLICATIONS

Bissett, D.L., et al., Photoprotective Effect of Superoxide Scavenging Antioxidants Against Ultraviolet Radiation–Induced Chronic Skin Damage In The Hairless Mouse, Photodermatol Photoimmunol Photomed 1990: 7: pp. 56–62.

Kligman, L.H., et al., Biochemical Changes in Hairless Mouse Skin Collagen After Chronic Exposure to Ultraviolet–A Radiation, Photochemistry and Photobiology vol. 54, No. 2, pp. 233–237, 1991.

Boyer, B., et al., UVA–and UVB–Induced Changes In Collagen And Fibronectin Biosynthesis in the Skin of Hairless Mice. J. Photochem. Photobiol. B: Biol., 14 (1992) pp. 247–159.

Bose, B. et al., Effect of UV–A on the Linolenic Acid Micelles, Radiation Research 133, pp. 340–344 (1993).

Zheng, P., et al., UVA–Induced Ultrastructural Changes in Hairless Mouse Skin: A Comparison of UVB–Induced Damage, The Society for Invesntigative Dermatology, Inc. 1993, pp. 194–199.

Longas, M., et al., Dietary Vitamin E Reverses the Effects of Ultraviolet Light Irradiation on Rat Skin Glycosaminoglycans, Biochimica et Biophysica Acta, 1156 (1993), pp. 239–244.

Bissett, D.L., et al., Wavelength Dependence of Histological, Physical, and Visible Changes in Chronically UV–Irradiated Hairless Mouse Skin, Photochemistry and Photobiology, vol. 50, No. 6, pp. 763–769, 1989.

Shaath, Nadim, Encyclopedia of UV Absorbers of Sunscreen Products, Cosmetics & Toiletries, Mar. 1987, vol. 102, No. 3, pp. 21–23.

Primary Examiner—Shelly A. Dodson

[57] ABSTRACT

The present invention relates to a method of protecting skin from the oxidative effects of ultraviolet A radiation including UVA-induced lipid peroxidation. The method comprises topically applying to the skin an effective amount of a photoprotective composition that contains a lipophilic antioxidant that does not have appreciable absorbance near wavelengths of 320–380 nm.

11 Claims, 24 Drawing Sheets

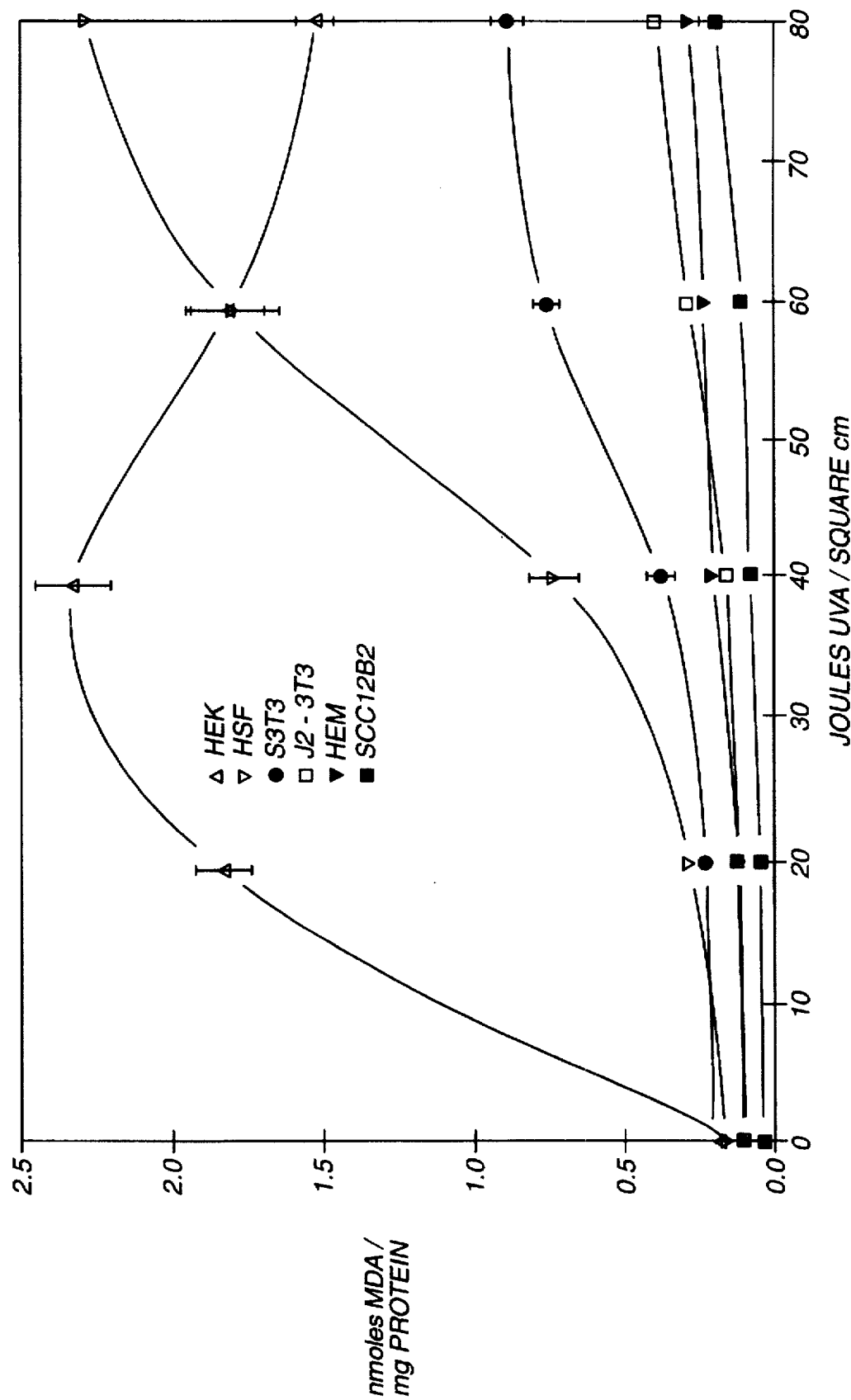

PHOTOPROTECTIVE LIPOPHILIC ANTIOXIDANT COMPOUNDS AND THEIR USE TO PREVENT UVA-MEDIATED LIPID PEROXIDATION

BACKGROUND OF THE INVENTION

1. Field of the Invention

The present invention relates to the protection of skin from the oxidative effects of ultraviolet (UV) A radiation. In particular, the present invention relates to photoprotective lipophilic antioxidant compositions and their use to prevent UVA-mediated oxidative effects including lipid peroxidation.

2. Background Information

The damaging effects of UV radiation, particularly sunlight, on skin are well known and documented. Indeed, exposure to solar radiation is known to cause a number of acute (i.e., erythema, pigmentation, and sunburn cell formation) and chronic (i.e. photodamage, aging and cancer) effects on skin.

Solar radiation that reaches the earth's surface contains UVA (320–400 nm) and some UVB (300–320 nm) wavelengths. A third component of solar radiation, UVC, is absorbed by the ozone layer above the earth before it reaches the earth's surface. The action spectra for most acute and chronic effects of solar exposure indicate that UVB wavelengths are more biologically active than UVA wavelengths [Shea et al., "Nonionizing radiation and the skin." In: *Physiology, Biochemistry, and Molecular Biology of the Skin*. 1991. LA Goldsmith, ed. Oxford University Press:New York. vol. 2, pp. 910–927; De Gruijl, et al., *Cancer Res* (1993) 53:53–60]. However, when the skin is protected from UVB the effects of UVA can be seen [Kligman et al., *Photochem Photobiol* (1991) 54:233–237; Zheng et al., *J Invest Dermatol* (1993) 100:194–199; Boyer et al., *J Photochem Photobiol B: Biol* (1992) 14:247–259; Bissett et al., *Photochem Photobiol* (1989) 50:763–769]. Thus, it is desirable to protect the skin against UVA radiation as well as the UVB portions of sunlight.

The mechanisms by which UV radiation produces its acute and chronic effects on skin are two fold: 1) direct absorption of energy by molecules of the skin, and 2) oxygen-dependent processes [Shea et al., "Nonionizing radiation and the skin." In: *Physiology, Biochemistry, and Molecular Biology of the Skin*. 1991. LA Goldsmith, ed. Oxford University Press:New York. vol. 2, pp. 910–927]. The first mechanism of UV radiation damage, direct absorption of energy by the skin, can be combated using sunscreens. Sunscreens, the most common agents employed to protect the skin from the effects of UV radiation, work by absorbing the UV radiation so that it does not penetrate the skin and cause damage. Thus, sunscreens provide protection against UV damage caused by direct absorption of energy by the skin. They do not, however, protect against damage caused by oxygen-dependent processes, the second mechanism by which UV radiation damages the skin unless they also incorporate UVA absorbing sunscreens. Even with the use of such sunscreens, however, there is evidence that sunscreens alone do not prevent all sun-induced alterations in skin, even when their use prevents skin erythema (sunburn) [Fischer et al., *Nature* (1996) 379:335–339], indicating that other, non-sunscreen agents which prevent aspects of sun-induced skin damage, should provide a measurable benefit in sun protection.

The second mechanism of UV radiation damage, oxygen-dependent processes, generally involves the production of reactive oxygen species as intermediates. Once produced, these reactive oxygen species cause pathology by a number of different mechanisms including the production of lipid peroxidation. Indeed, the production of free radicals and lipid peroxidation has been associated with characteristic changes associated with aging in many tissues including the skin [Machlin, et al., *FASEB J* (1987) 1:441–445; Emerit, I. "Free radicals and aging in skin." In: *Free Radicals and Aging*. 1992. I Emerit and B Chance, eds. Birkhauser Verlag Base: Switzerland, pp. 328–341; De Quiroga et al., "Relationship between antioxidants, lipid peroxidation and aging." In: *Free Radicals and Aging*. 1992. I Emerit and B Chance, eds. Birkhauser Verlag Base: Switzerland, pp. 109–123; Yagi, K., "Lipid peroxides in the skin." In: *The Biological Role of Reactive Oxygen Species in the Skin*. 1987. O. Hayaishi, S. Imamura, Y. Miyachi, eds. Elsevier: New York, pp. 109–116].

The apparent importance of this second mechanism of UV radiation damage supports the use of antioxidant supplementation as a means of photoprotection. A large number of reported studies have examined the effects of various agents, including antioxidants, on the effects of UVA [Bose et al., *Radiat Res* (1993) 133:340–344; Longas et al., *Biochem Biophys Acta* (1993) 1156:239–244; Bissett et al., *J Soc Cosmet Chem* (1992) 43:85–92; Bissett et al., *Photodermatol Photoimmunol Photomed* (1990) 7:56–62; Leccia et al., *Photochem Photobiol* (1993) 58:548–553; Gaboriau et al., *Photochem Photobiol* (1993) 58:515–520], UVB [Pelle et al., *Arch Biochem Biophys* (1990) 283:234–240; 240; Danno et al., *J Invest Dermatol* (1984) 83:166–168; Bissett et al., *J Soc Cosmet Chem* (1992) 43:85–92; Darr et al., *Brit J Dermatol* (1992) 127:247–253; Hamanaka et al., *J Dermatol* (1990) 17:595–598; Koone et al., *J Invest Dermatol* (1986) 87:343–347; Black et al., *Photochem Photobiophys* (1980) 1:119–123; Peterson et al., *J Invest Dermatol* (1980) 75:408–410; Kono et al., *J Dermatol* (1992) 19:389–392; Black et al., *Photochem Photobiol* (1984) 40:69–75; Black et al., *Photochem Photobiol* (1991) 53:707–716; Black et al., *Photochem Photobiol* (1986) 43:403–408, Bissett et al., *Photodermatol Photoimmunol Photomed* (1990) 7:56–62], UVC [Pelle et al., *Arch Biochem Biophys* (1990) 283:234–240] or PUVA [Darr et al., *Brit J Dermatol* (1992) 127:247–253] in liposomes [Pelle et al., *Arch Biochem Biophys* (1990) 283:234–240; Bose et al., *Radiat Res* (1993) 133:340–344], cultured human skin fibroblasts[Leccia et al., *Photochem Photobiol* (1993) 58:548–553; Gaboriau et al., *Photochem Photobiol* (1993) 58:515–520], mice [Danno et al., *J. Invest Dermatol* (1984) 83:166–168; Bissett et al., *J Soc Cosmet Chem* (1992) 43:85–92; Trevethick et al., *Arch Biochem Biophys* (1992) 296:575–582; Koone et al., *J Invest Dermatol* (1986) 87:343–347, Black et al., *Photochem Photobiophys* (1980) 1:119–123, Peterson et al., *J Invest Dermatol* (1980) 75:408–410, Kono et al., *J Dermatol* (1992) 19:389–392, Black et al., *Photochem Photobiol* (1984) 40:69–75, Black et al., *Photochem Photobiol* (1991) 53:707–716, Black et al., *Photochem Photobiol* (1986) 43:403–408, Bissett et al., *Photodermatol Photoimmunol Photomed* (1990) 7:56–62], pigs[Darr et al., *Brit J Dermatol* (1992) 127:247–253], guinea pigs [Hamanaka et al., *J Dermatol* (1990) 17:595–598] or rats [Longas et al., *Biochem Biophys Acta* (1993) 1156:239–244]. Though a considerable number of agents has been tested for in vivo effects on UVB, evidence exists only for vitamin E as an agent to prevent UVA-induced effects in animals[Longas et al., *Biochem Biophys Acta* (1993) 1156:239–244]. Oral alpha-tocopherol has been shown to prevent UVA-induced alterations in glycosaminoglycans in rats [Longas et al., *Biochem*

Biophys Acta (1993) 1156:239–244], but no effect of topical vitamin E was seen on UVA-induced skin sagging in hairless mice [Bissett et al., *Photodermatol Photoimmunol Photomed* (1990) 7:56–62]. Thus, a general means of preventing UVA-induced oxidative effects has not been provided. However, such a means would be desirable.

SUMMARY OF THE INVENTION

Therefore, it is an object of the present invention to provide means and methods of protecting the skin from the oxidative effects caused by exposure to UVA radiation.

It is another object of the present invention to provide a topical composition that, when applied to human skin, protects against UVA-induced oxidative effects including lipid peroxidation.

The present invention results from the surprising discovery that certain lipophilic antioxidants, when applied to skin, protect the skin against the adverse effects of UVA-induced lipid peroxidation. In one embodiment, the present invention relates to a method of protecting mammalian skin from oxidative effects of UVA radiation. The method comprises topically applying to the skin a safe and effective amount of a lipophilic antioxidant that does not have appreciable absorbance at or near a wavelength of 345 nm.

Various other objects and advantages of the present invention will become apparent from the drawings and the following description of the invention.

BRIEF DESCRIPTION OF THE DRAWINGS

FIG. 12 shows the effect of UVA exposure on the production of lipid peroxidation by various cell types in monolayer culture. Human epidermal keratinocytes (HEK), human skin fibroblasts (HSF), Swiss 3T3 mouse fibroblasts (S3T3), J2-3T3 mouse fibroblasts (J2-3T3), human epidermal melanocytes (HEM) and human squamous cell carcinoma cells (SCC12B2) were exposed to increasing doses of UVA using only Sylvania F40 350BL lamps (98% UVA). The average number of milligrams protein per plate for each cell type (standard deviation) was: HEK=5.3 (0.2); HSF=1.1 (0.1); S3T3=1.9 (0.2); J2-3T3=3.2 (0.1); HEM=1.2 (0.2); SCC12B2=5.1 (0.5).

DETAILED DESCRIPTION OF THE INVENTION

Figure 1:
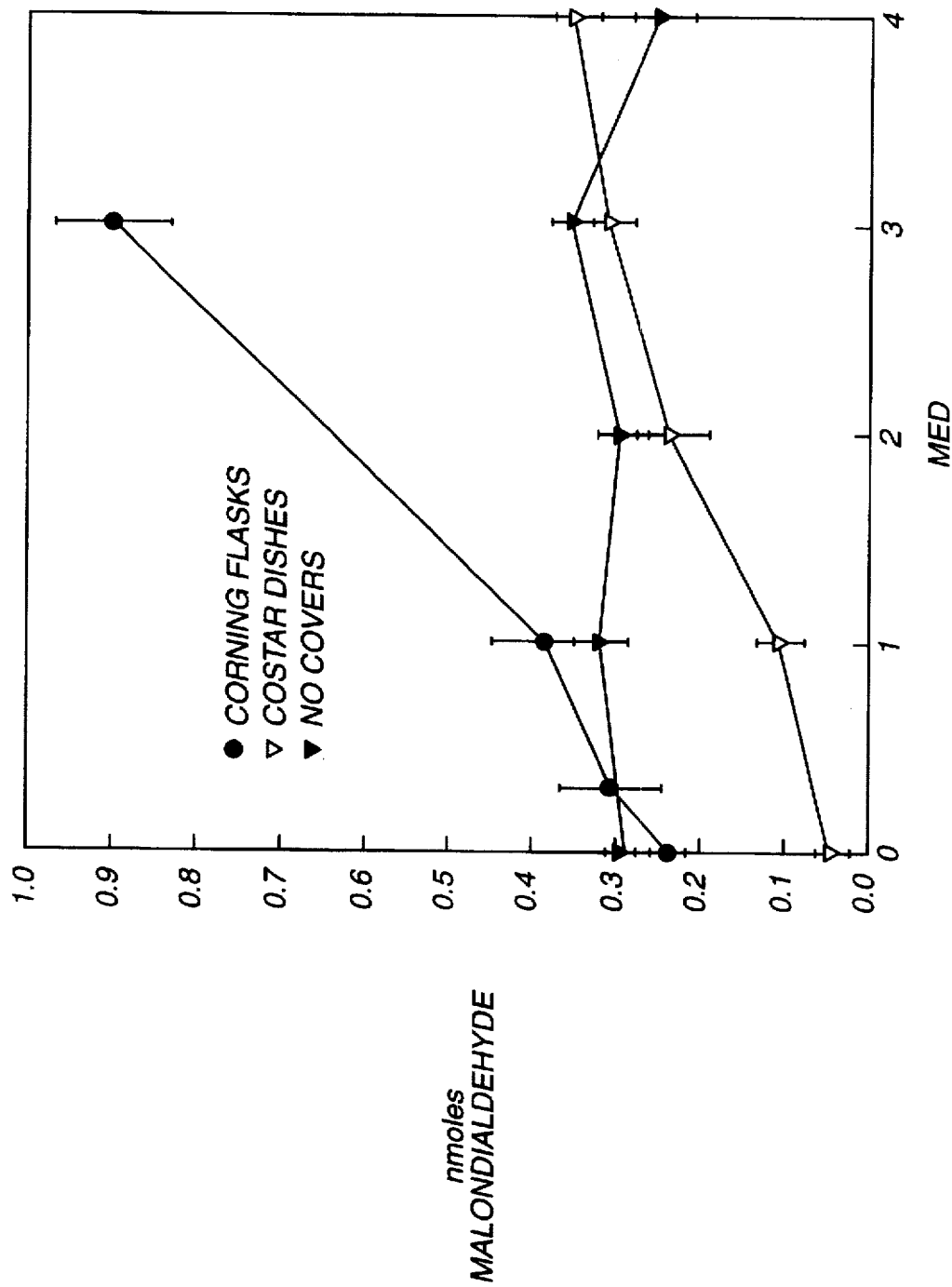
FIG. 1 shows the effect of different culture plates on the production of lipid peroxidation by human dermal fibroblasts exposed to solar simulated light. Cells were exposed to solar simulated light through the covers on Corning 75 $cm^2$ flasks or through Costar 100 mm tissue culture dishes with or without the covers. Triplicate cultures were exposed to increasing numbers of MED using the solar simulator arrangement of lamps.

The present invention is directed to methods of protecting skin from the oxidative effects of UVA radiation including UVA-induced lipid peroxidation. The present invention is also directed to a protective composition for topical application to skin of humans and like susceptible animals. The present invention results from the surprising discovery that certain lipophilic antioxidants when applied to skin cells protect these cells against the adverse oxidative effects of UVA radiation, including UVA-induced lipid peroxidation.

In the method of the present invention, skin cells are protected from the oxidative effects of UVA radiation by topically applying to such cells an effective amount of a photoprotective composition that contains a lipophilic antioxidant. The lipophilic antioxidants employed in the composition do not have any appreciable absorbance (i.e., offer no significant sunscreen benefits) at or near wavelengths of 320–380 nm, especially wavelengths near 345 nm.

Antioxidants that are both lipophilic and do not absorb at wavelengths which would have made them susceptible to forming oxygen-derived free radicals themselves have been found to be effective at preventing skin damage caused by UVA-induced oxidative effects.

That the antioxidant must be lipophilic to protect against UVA-induced oxidative damage is evidenced by the results shown herein with ascorbic acid versus ascorbyl-6-palmitate. By simply adding a lipophilic moiety to ascorbic acid, the effect on UVA-induced lipid peroxidation went from one extreme to the other. Hydrophilic ascorbic acid acted synergistically with UVA to induce additional lipid peroxidation. However, lipophilic ascorbyl palmitate was one of the most effective agents tested in preventing UVA-induced lipid peroxidation. The differences in the two molecules do not involve changes in their activity as antioxidants, only the environment in which they reside.

In addition to being lipophilic, the antioxidants used in the present method must not absorb appreciably in the UVA portion of the spectrum. α-napththol, which consistently produced unusual results in both cell types tested as described below, also absorbed the furthest into the UVA region of the antioxidants tested.

Preferred lipophilic antioxidants include, but are not limited to, ascorbyl-6-palmitate, butylated hydroxyanisole (BHA) and butylated hydroxytoluene (BHT). Ascorbyl palmitate has previously been shown to be ineffective at preventing UVB induced wrinkling in hairless mice[Bissett et al., *Photodermatol Photoimmunol Photomed* (1990) 7:56–62], however it has been shown to protect endothelial cells from the cytotoxic effects of products of lipid peroxidation[Kaneko et al., *Arch Biochem Biophys* (1993) 304:176–180]. No examination of the effect of ascorbyl-palmitate on UVA-mediated events has been reported.

BHA has also been shown to be effective at preventing UVC-induced lipid peroxidation in liposomes [Pelle et al., *Arch Biochem Biophys* (1990) 283:234–240]. Additionally, BHA has been found to be effective at preventing UVB- or PUVA-induced ornithine decarboxylase activity (associated with tumor formation) [Kono et al., *J Dermatol* (1992) 19:389–392; Black et al., *Photochem Photobiol* (1986) 43:403–408], however, BHA had no effect on UVB-induced photocarcinogenesis[Black et al., *Photochem Photobiol* (1986) 43:403–408]. No results concerning the effects of BHA on other UVA-mediated events have been reported.

Of the three preferred lipophilic antioxidants, BHT has seen the greatest amount of study. A great deal of literature exists concerning the ability of oral ingestion of BHT to provide protection against the acute and chronic effects of UVB exposure [Koone et al., *J Invest Dermatol* (1986) 87:343–347; Black et al., *Photochem Photobiophys* (1980) 1:119–123; Peterson et al., *J Invest Dermatol* (1980) 75:408–410; Black et al., *Photochem Photobiol* (1984) 40:69–75; Black et al., *Photochem Photobiol* (1991) 53:707–716; Black et al. *Photochem Photobiol* (1986) 43:403–408] including photocarcinogenesis, erythema and induction of ornithine decarboxylase activity. In addition, BHT has been shown to be effective in preventing UVA-[Bose et al., *Radiat Res* (1993) 133:340–344] and UVC [Pelle et al., *Arch Biochem Biophys* (1990) 283:234–240] induced lipid peroxidation in liposomes. No evidence of activity of BHT against the characteristic changes involved in photoaging or against UVA-induced changes in animals or cultured cells has been reported.

In the present invention the photoprotective composition containing a lipophilic antioxidant is applied topically to skin cells to protect the skin from the oxidative effects of UVA radiation. Preferably, the composition is applied prior to exposure to the sun.

The amount of the lipophilic antioxidant present in the compositions and applied to the skin cells may vary so long as enough of the antioxidant is present to prevent UVA-mediated oxidative damage including lipid peroxidation. Preferably, the antioxidant is present in the composition from about 0.0001% to about 10% (w/w), more preferably from about 0.01% to about 1%, and more preferably still from about 0.1% to about 0.5%.

The photoprotective compositions of the present invention may be made into a variety of product types. The photoprotective compositions can be in solid, liquid or aerosol form so long as they are suitable for topical administration. For example, the compositions can be formulated into a liposomal formulation, an emollient, a liquid, a cream, a gel, an ointment, a microemulsion, or a solution. The compositions of the present invention can also be incorporated into various cosmetic and personal care products such as hand and body lotions, oils, ointments, lip balms and facial cosmetics.

Photoprotective compositions suitable for use in the protective method of the present invention can also contain other photoprotective agents such as sunblocks or sunscreens. Indeed, skin protection against sun damage may be optimized by using a combination of a lipophilic antioxidant to prevent UVA-induced oxidative damage of the present invention with a sunblock or a sunscreen to prevent direct absorption of energy by the skin cells.

Conventional sunblocks and sunscreening agents are suitable for use in the present invention. Examples of sunblocks suitable for use in the present invention include, but are not limited to, zinc oxide and titanium dioxide. Suitable sunscreening agents include, for example, p-aminobenzoic acid and its derivatives, anthranilates, salicylates, cinnamates and their derivatives, naphtholsulfonates, benzophenones, dibenzoylmethane derivatives, and tannic acid and its derivatives. For a list of numerous suitable agents see *Cosmetics & Toiletries*, published by Allured Publishing Corporation, for example, Vol. 102, March 1987, pp. 21–40.

A safe and effective amount of sunblock and/or sunscreen can be included in the photoprotective compositions of the present invention. Generally, compositions of the present invention may contain from about 1 to about 15% (w/w) of a sunblock or sunscreening agent, in accordance with FDA-OTC Panel recommendations.

Other conventional and typical skin care product additives may also be included in the photoprotective compositions. Various vitamins may also be included in the photoprotective compositions of the present invention. Examples of such vitamins include, but are not limited to, Vitamin A and derivatives thereof, Vitamin $B_2$, biotin, pantothenic, Vitamin D, Vitamin E and combinations thereof.

The following examples are included to further illustrate the practice of this invention, and are not meant to be limiting in anyway.

EXAMPLES

Cell cultures

Monolayer cultures of mouse Swiss 3T3 (S3T3) and J23T3 fibroblasts, human epidermal melanocytes (HEM), human dermal fibroblasts (HSF), human epidermal keratinocytes (HEK) and a human squamous cell carcinoma cell line (SCC12B2) were grown to confluence in the appropriate media as follows. S3T3 cells, J2-3T3 cells and HSF were grown in Dulbecco's modified Eagle medium (DMEM) containing 10% calf serum. HEM were grown in Clonetics melanocyte growth medium. HEK and SCC12B2 cells were grown in an epidermal growth medium containing 3:1 high glucose DMEM to Ham's F12 supplemented with 2 µg/ml hydrocortisone, $5 \times 10^{-10}$ M cholera toxin, 25 µg/ml insulin, 25 µg/ml transferrin, and $1 \times 10^{-10}$ M triiodothyronine. HEK were grown on a feeder layer of mitomycin C treated Swiss 3T3 fibroblasts as described [Rheinwald et al., *Cell* (1975) 6:331-344].

Example 1

Effect of culture materials on the production of lipid peroxidation

To determine whether solar simulated light could produce oxidative effects on cells in culture, neonatal human dermal fibroblasts were irradiated using a combination of Sylvania F40 350BL lamps (98% UVA) and Westinghouse FS40 Sunlamps (approximately 50% UVA, 50% UVB) to simulate the normal solar spectrum.

Neonatal human dermal fibroblast cultures were grown as described above in Corning 75 $cm^2$ tissue culture flasks or in 100 mm Costar culture dishes. Cultures were then irradiated through the use of a solar simulator arrangement of bulbs with a 6:5 mix of Sylvania F40 350BL lamps and Westinghouse FS40 Sunlamps (50% UVA, 50% UVB).

Following irradiation, a lipid peroxidation assay was conducted. Briefly, irradiated plates were scraped with a rubber policeman and cells and solution were homogenized on a dounce homogenizer. An aliquot of the protein extract was taken for Lowry determination of total protein [Lowry et al., *J Biol Chem* (1951) 193:265-275]. The remainder of the extract was precipitated with trichloroacetic acid. The supernatant was assayed for malondialdehyde content in duplicate by combining it with 0.5% thiobarbituric acid solution before boiling for 30 minutes. Samples were measured for their absorbance at 532 nm. Malondialdehyde levels were determined using the reported extinction coefficient[Wilbur et al., *Arch Biochem Biophys* (1949) 23:305-313].

When cultures were grown in Corning 75 $cm^2$ tissue culture flasks, a dose-dependent increase in the level of malondialdehyde was produced (FIG. 1) indicative of an increase in the level of cellular lipid peroxidation. When cells were grown in Costar 100 mm culture dishes the levels of lipid peroxidation were reduced compared to Corning flasks when irradiated at equivalent doses of UV (FIG. 1). When cells were irradiated with the lids of the Costar dishes removed, no effect of UV was seen on the levels of lipid peroxidation in irradiated cells at the doses tested (FIG. 1).

In order to understand the different results produced by the use of different culture materials, the spectra of the light penetrating the different culture plates were examined. The spectral power distribution of the Sylvania F40 350BL fluorescent lamps used to irradiate the cells was measured with an Optronics Model 742 Spectroradiometer at 2 nm intervals between 250 and 400 nm. The irradiance was multiplied by the transmission of the Costar lid used to cover the cells at each wavelength to determine the irradiance of the source to the cells. The irradiance at each wavelength was multiplied with a scaler value (representing time) such that the integral equaled 80 $J/cm^2$.

Figure 2:
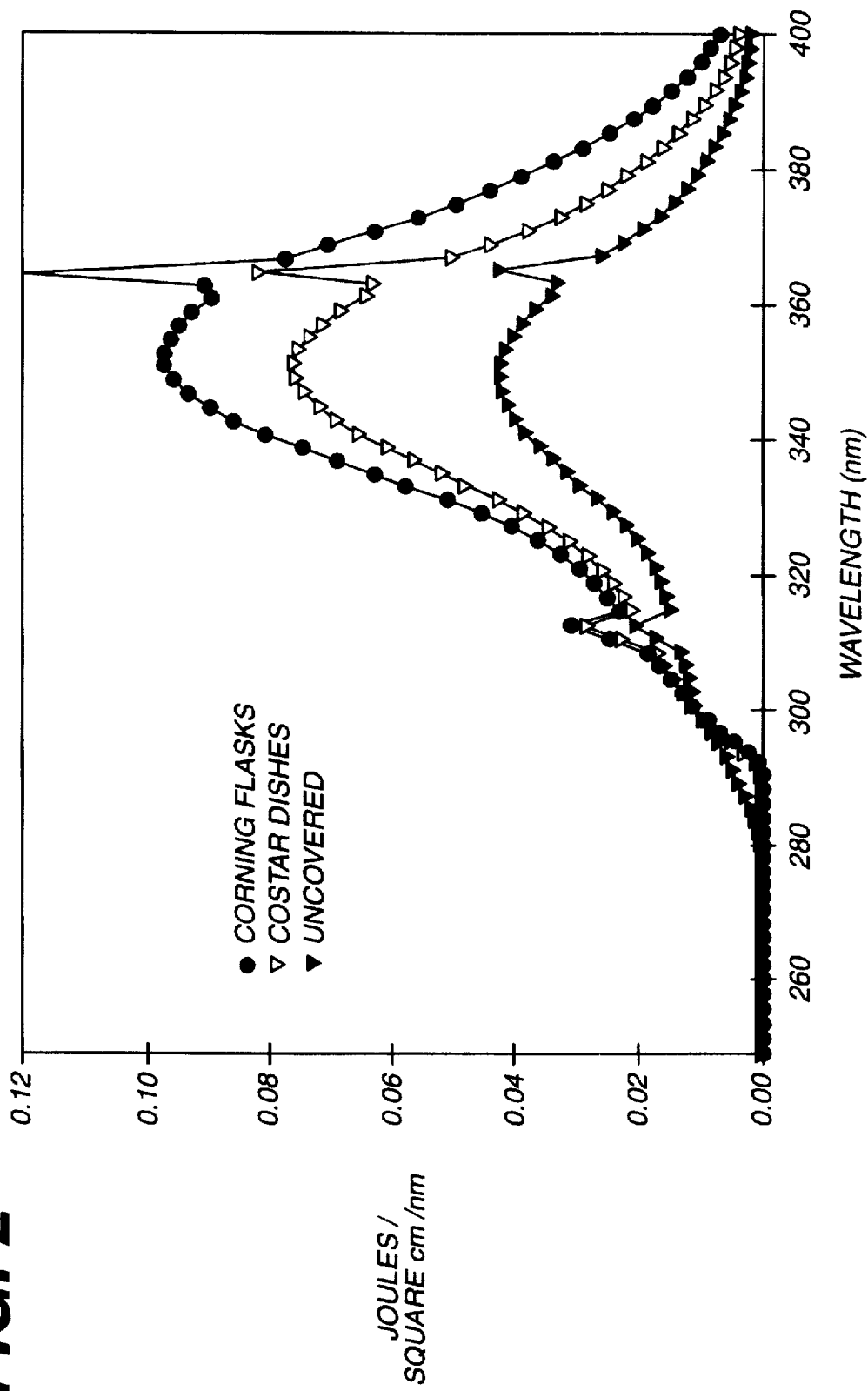
FIG. 2 shows the spectral dose distribution of light sources with different culture materials. The spectral dose distribution is presented for the three cell culture conditions identified in the lipid peroxidation measurements described previously (see FIG. 1) using the solar simulator arrangement of lamps.

The spectral dose distribution is presented (FIG. 2) for the three cell culture conditions identified in the lipid peroxidation experiments (FIG. 1) using the solar simulator arrangement of lamps described above. Under these conditions, the Corning flasks received 40% more UVA than the Costar dishes with the equivalent amounts of UVB.

Figure 3:
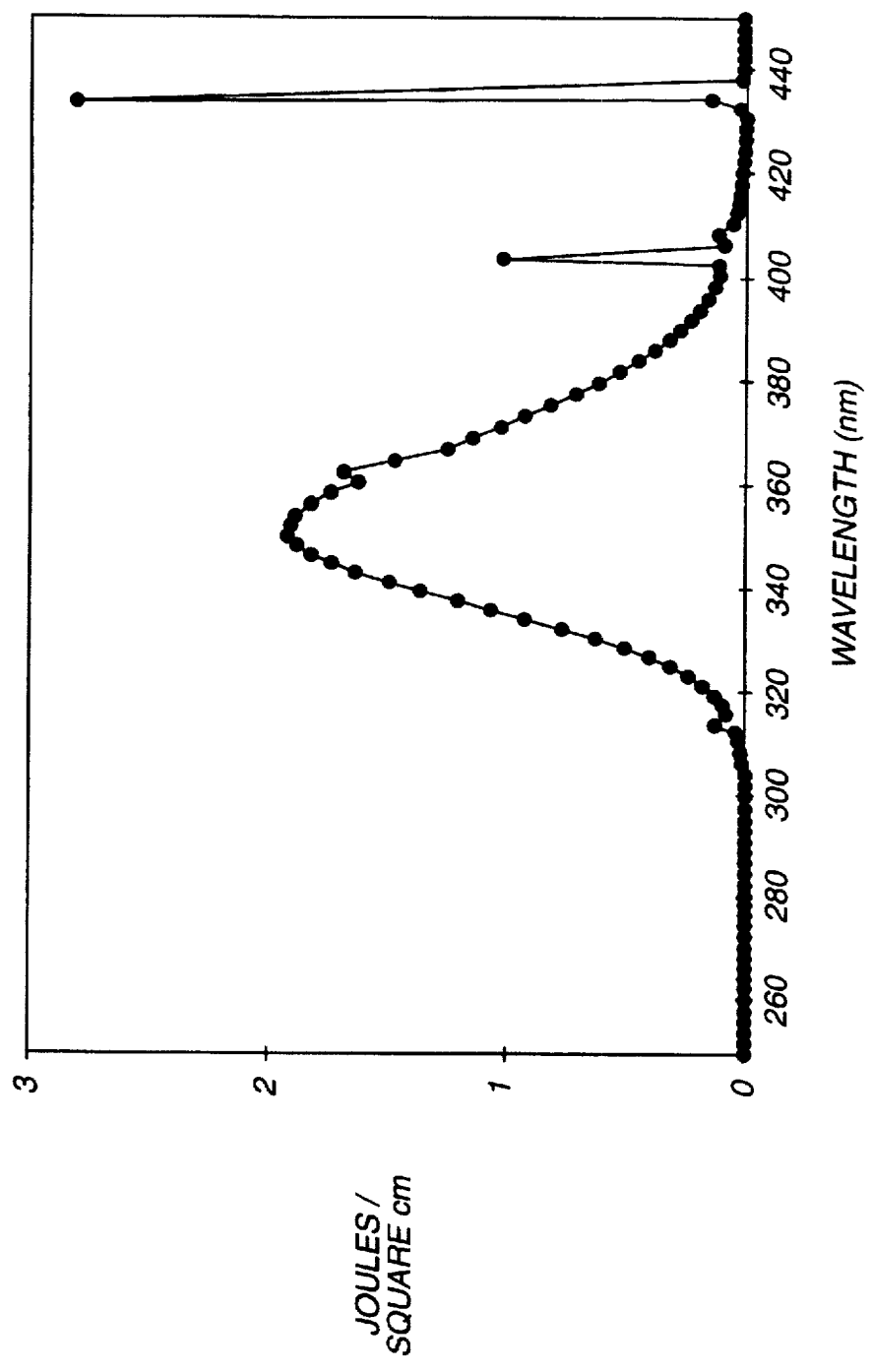
FIG. 3 shows the spectral irradiance of F40 350BL lamps. The spectral irradiance for the Sylvania F40 350BL lamps (98% UVA, 2% UVB) is presented.

The uncovered dishes received even less UVA (Corning flasks received 140% more UVA than uncovered Costar dishes). These results indicate a likely role for UVA selectively to induce lipid peroxidation in these cultured cells. Consequently, all subsequent experiments (except where noted) were performed using only the Sylvania F40 350Bl lamps (see FIG. 3 for spectral irradiance using these lamps) since they produce spectra composed of 98% UVA with little contribution from UVB (2%).

Example 2

Determination of the action spectrum for the production of lipid peroxidation

Figure 4:
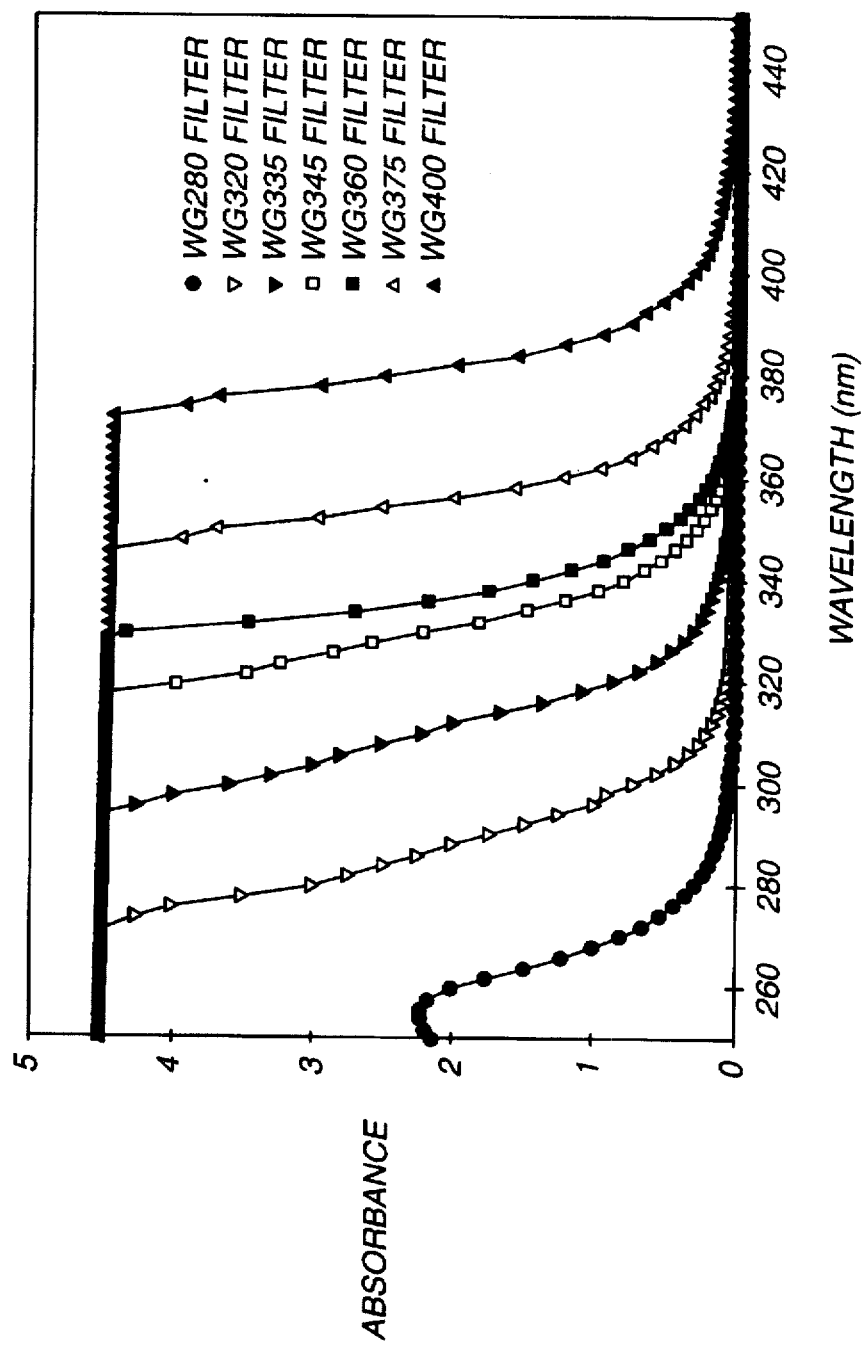
FIG. 4 shows the absorbance spectra of Schott filters. The absorbance of various WG filters was determined and is shown.

To determine the portion of the spectra produced by the F40 350BL lamps that was responsible for inducing lipid peroxidation, confluent cultures of HSF and S3T3 cells grown in 60 mm culture dishes were irradiated through the lids using the Sylvania F40 350BL lamps as described above with the addition of a number of Schott filters which absorb varying amounts of energy at varying wavelengths as shown in FIG. 4.

Action spectra were determined by using a series of long pass filters to evaluate the differences in dose between two adjacent filters, and attributing the differences in the response being evaluated between the two filters to that waveband in proportion to the total energy difference between the two filters. The spectral dose distributions of adjacent filters were subtracted from each other to determine the difference in spectral dose. This was done for each adjacent pair of filters. These difference dose distributions were integrated to determine the difference dose band (See FIG. 6).

The level of lipid peroxidation per unit protein content for each filter pair was determined as described above. The differences in lipid peroxidation for each filter pair was determined by subtracting the levels for the adjacent pair. The peroxidation differences for a filter pair were divided by the difference dose band to determine the level of peroxidation attributable to each unit dose of the difference band, indicating the absolute sensitivity of peroxidation to that wave band. The absolute sensitivities of all wavebands were integrated and each of the individual sensitivities were divided by the sum to determine the percentage of sensitivity of each waveband. The relative sensitivities were plotted as a function of the difference wavelength band to indicate which portion of the UV spectrum was most effective in causing lipid peroxidation.

Spectral absorbance of each of the Schott long pass filters used for the action spectra determination was measured using a Cary 2300 Spectrophotometer with diffuse reflectance accessory. Absorbances at wavelength between 250 and 400 nm in 2 nm intervals were converted to percent transmission. To determine the spectral dose distribution delivered to the filtered cells, the spectral dose distribution of the source with the Costar lid was multiplied at each wavelength with the transmission of the appropriate Schott filter. Each of these distributions was also integrated to determine the total energy delivered through the filter to the cells. The absorbance of these filters demonstrates the pattern of increased absorbance to higher wavelengths with successive filters.

Figure 5:
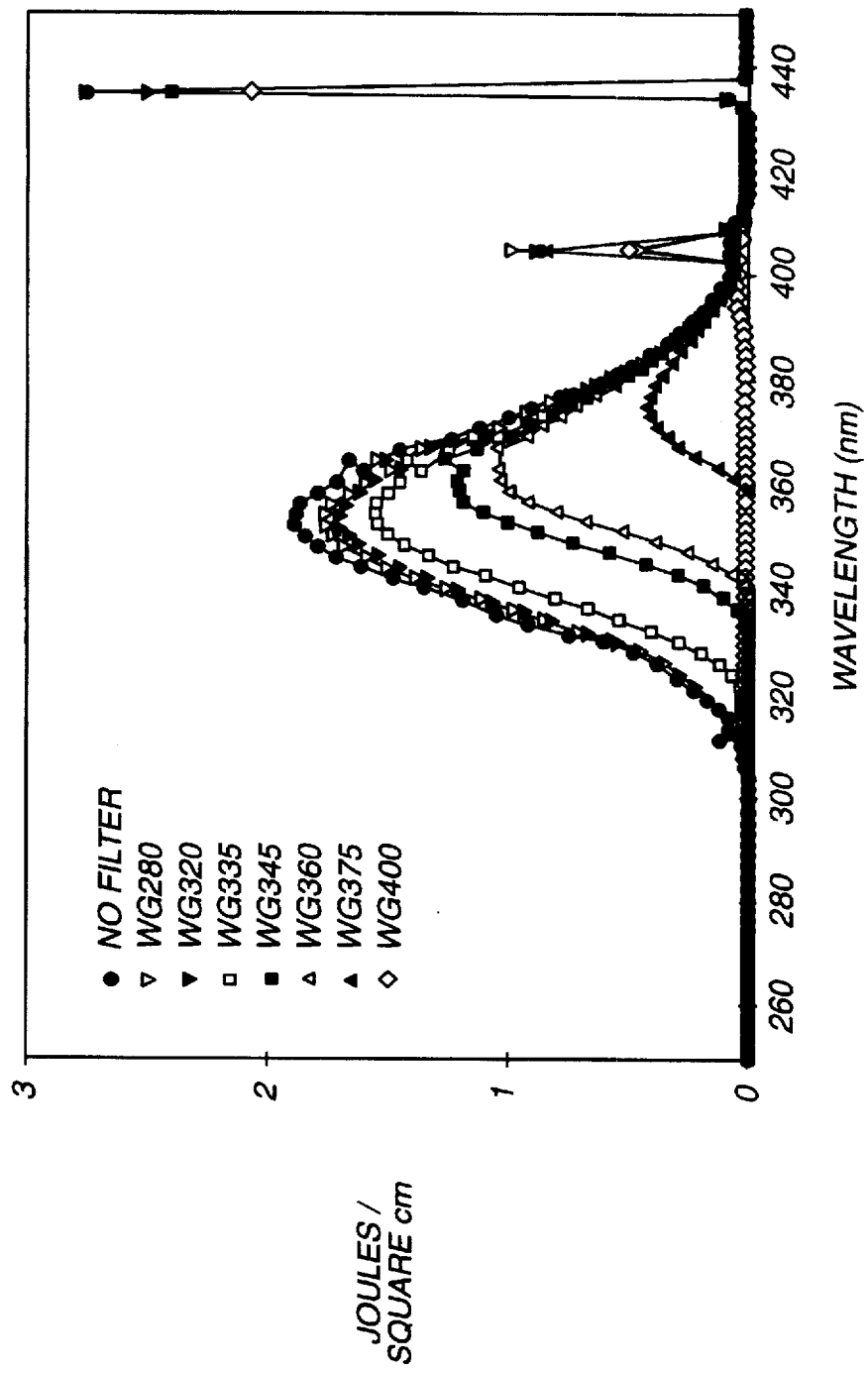
FIG. 5 shows the spectral dose distribution produced with the Schott Filters described in FIG. 4.

The resultant spectral dose distribution after subtracting the absorbance of each filter from the spectra produced by the lamps is shown in FIG. 5. As shown, the use of the filters with increasing wavelength number shifts the absorbance maximum of the resulting spectra to higher wavelengths and eliminates the radiation at lower wavelengths.

The difference in the spectra from one filter to the next (FIG. 6) is used to determine the amount of lipid peroxidation involved in each step from one filter to the next.

Figure 6:
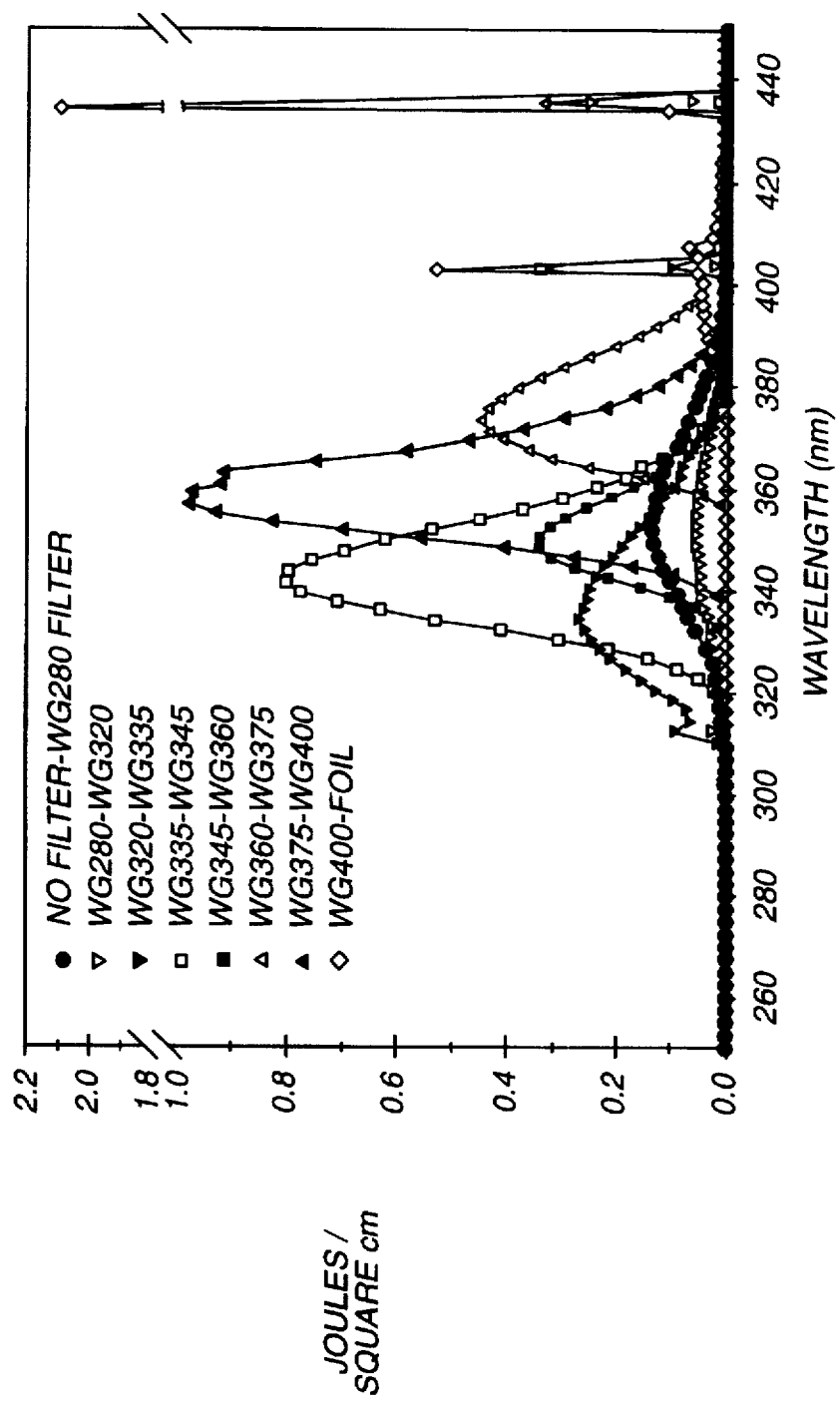
FIG. 6 show the difference spectra produced using the Sylvania F40 350BL fluorescent lamps in combination with the Schott Filters described in FIGS. 4 and 5. These spectra represent the differences in spectra produced when comparing one filter to the next in the series.
Figure 7:
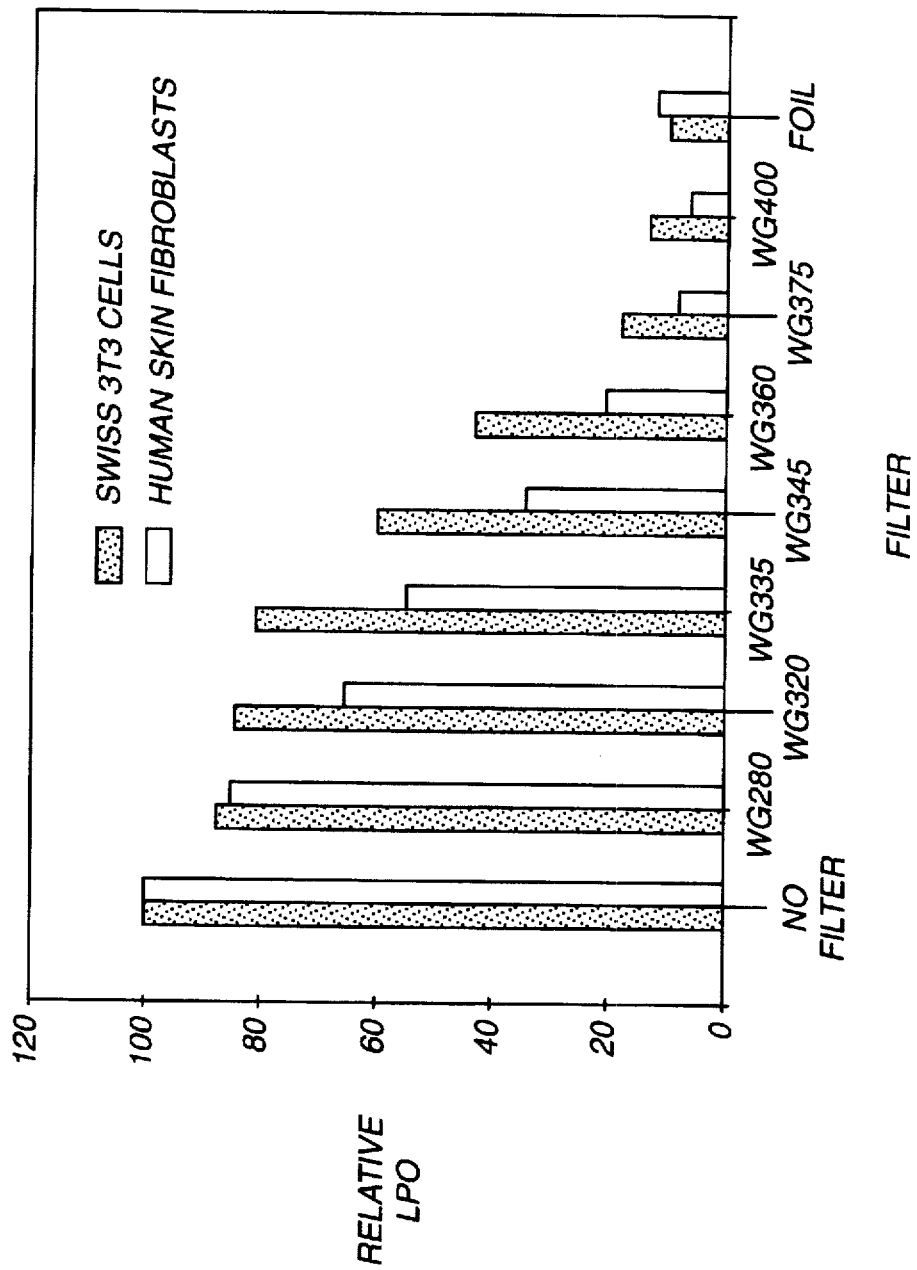
FIG. 7 shows lipid peroxidation produced in human dermal fibroblasts (HSF) and Swiss 3T3 cells (S3T3) in the presence or absence of the Schott Filters described in FIGS. 4–6.
Figure 8:
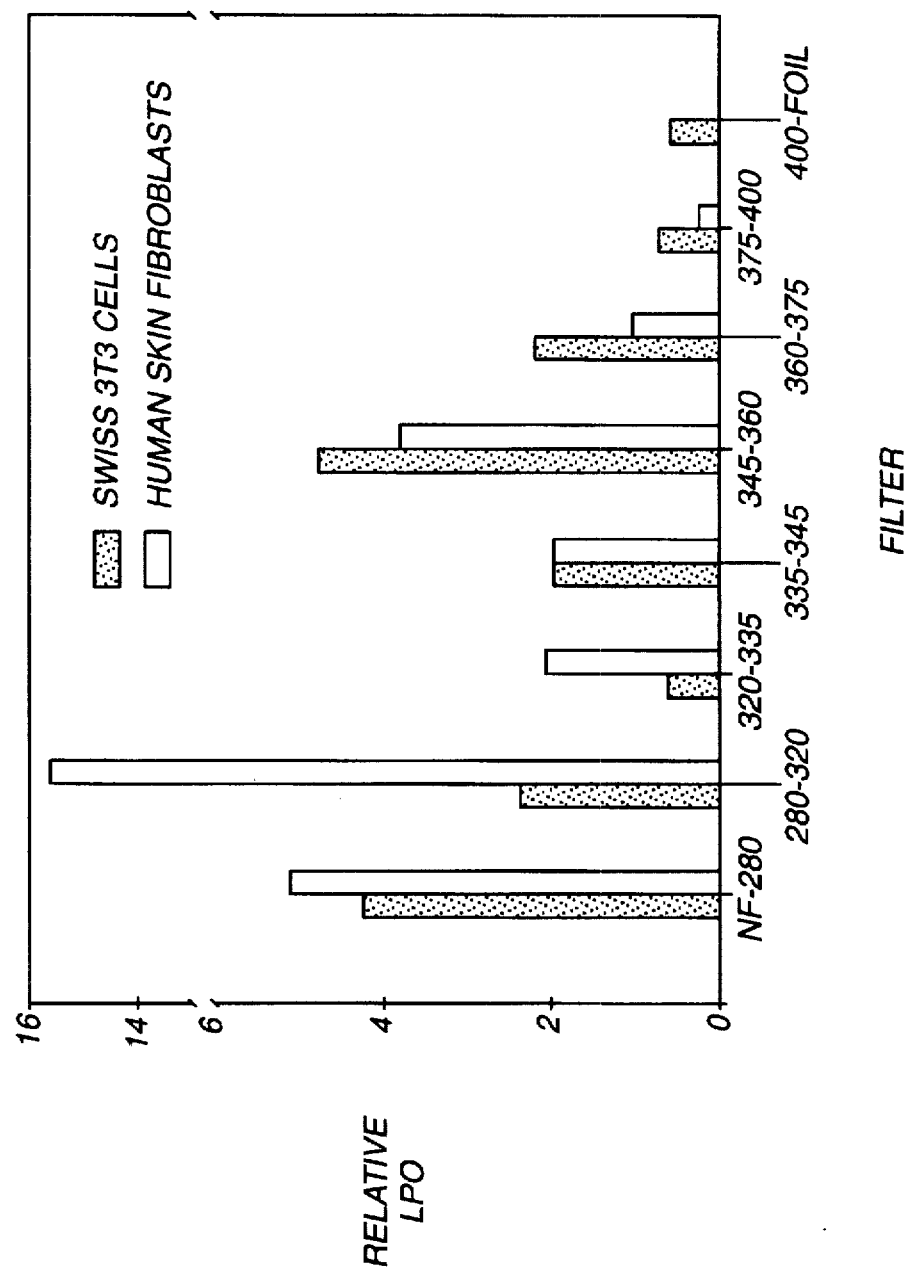
FIG. 8 shows lipid peroxidation action spectrum for human dermal fibroblasts (HSF) and Swiss 3T3 Mouse Fibroblasts (S3T3). These action spectra were determined using the information from FIGS. 6 and 7.

The amount of lipid peroxidation produced using the filters described in FIGS. 4–6 is shown in FIG. 7. As indicated, the levels of lipid peroxidation decline with the use of filters with increasing wave number and absorbance into higher wavelengths in the UVA region of the spectrum. To determine the contribution of each filter to the effect on lipid peroxidation, the change in lipid peroxidation per change in filter must be divided by the difference spectra produced by successive filters (FIG. 6). The result of this calculation is shown in FIG. 8 and represents the contribution of each portion of the spectra to the effect on lipid peroxidation seen using the Sylvania F40 350BL fluorescent lamps.

As indicated, the change in lipid peroxidation produced when the WG280 filter is used compared to no filter represents a region of the spectra which is important for the production of lipid peroxidation in human dermal fibroblasts and Swiss 3T3 cells. Additionally, the change from WG345 filter to the WG360 filter also represents a region which contributes significantly to this effect. The difference spectra for each of these transitions produce a peak with absorbance maximum very close to 345 nm indicating that a chromophore exists which is important for the UV-dependent production of lipid peroxidation which has an absorbance maximum very close to 345 nm. Interestingly, difference spectra with peaks closely adjacent to the two identified peaks are less sensitive and help to specifically identify the important wavelengths in the UVA region of the spectrum.

Figure 9:
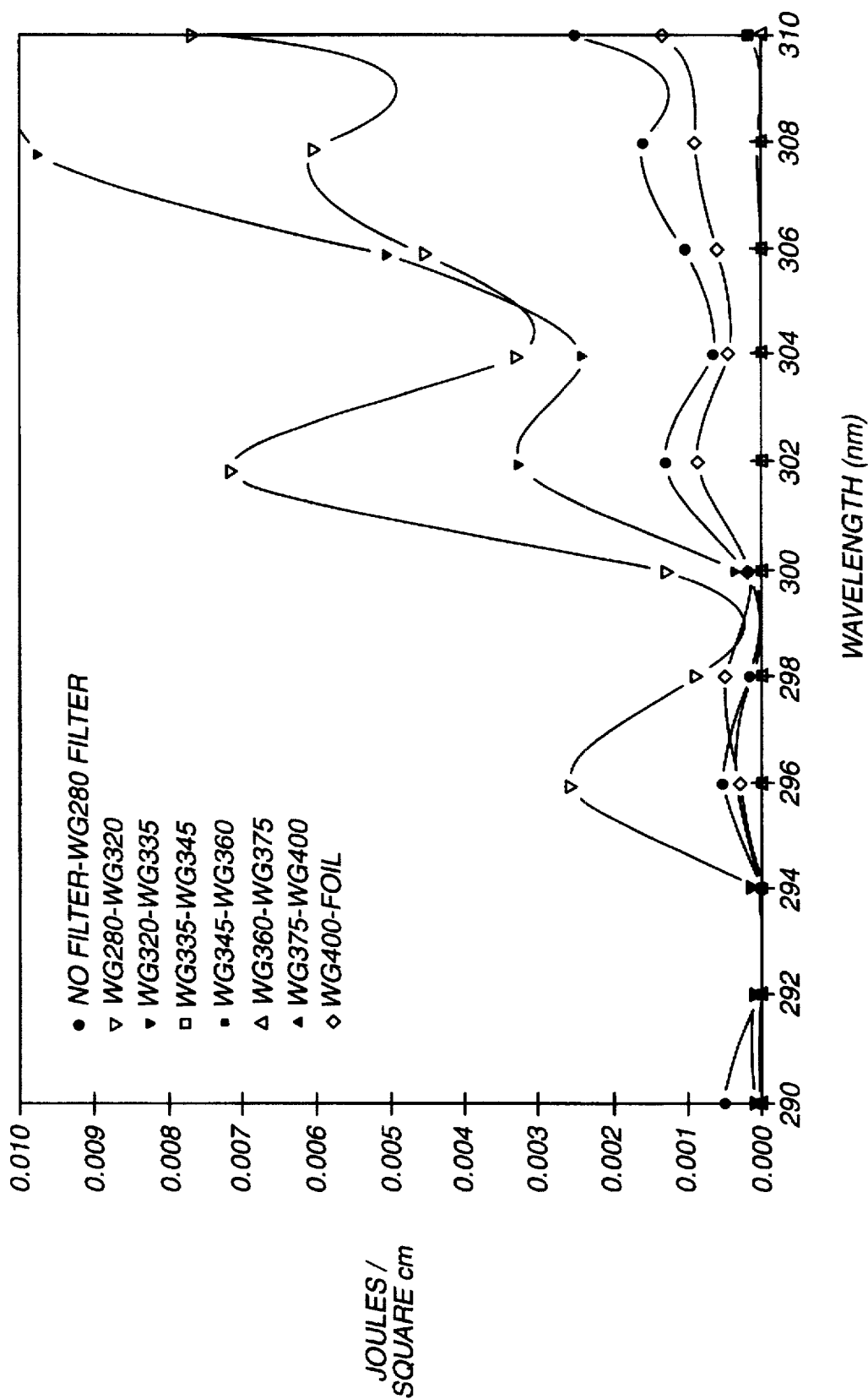
FIG. 9 shows difference spectra produced using the Sylvania F40 350BL fluorescent lamps as described in FIG. 6. This presentation highlights selected wavelengths (290–310 nm) from FIG. 6.
Figure 10:
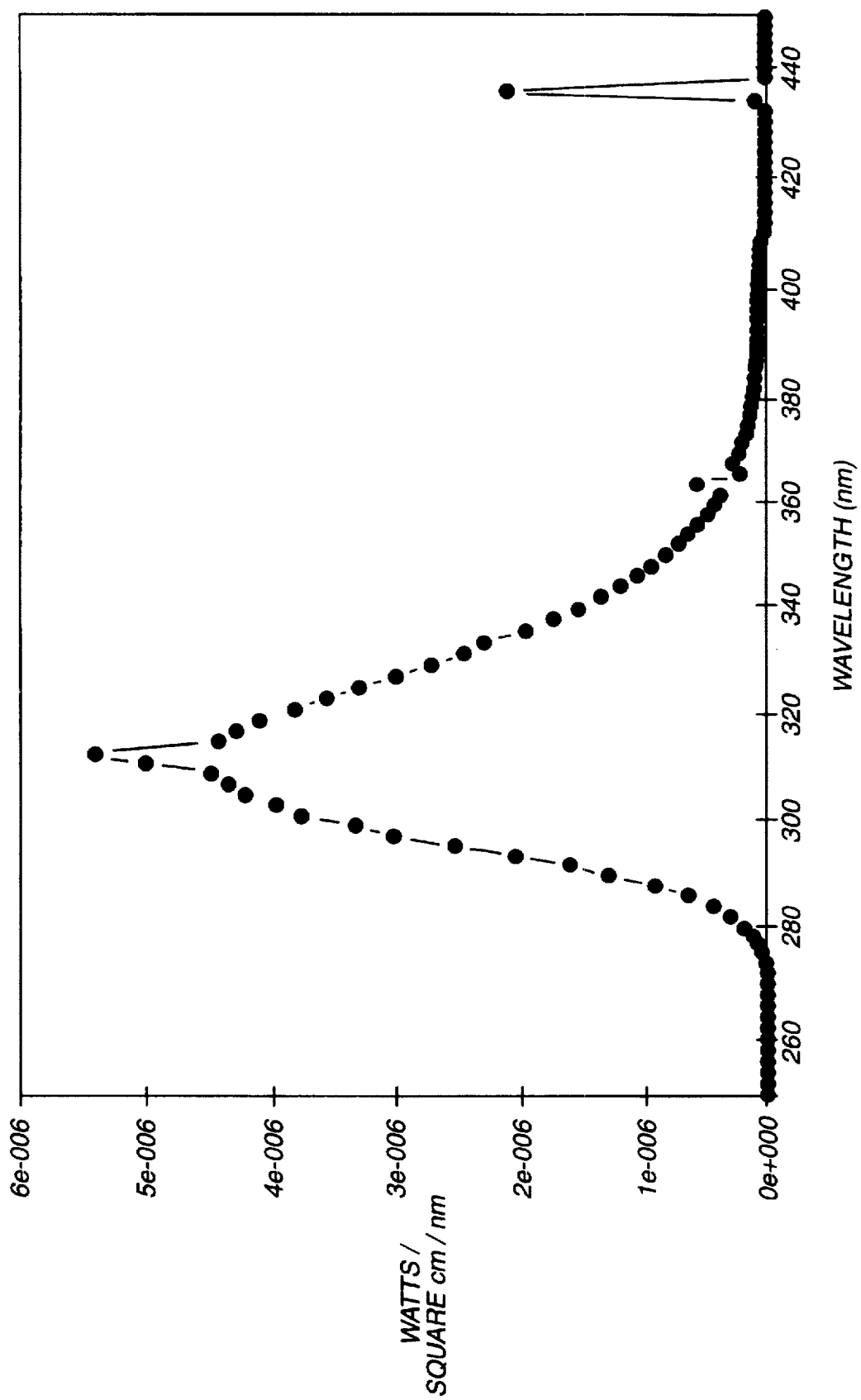
FIG. 10 shows the spectral irradiance of Westinghouse FS40 Sunlamps alone.
Figure 11:
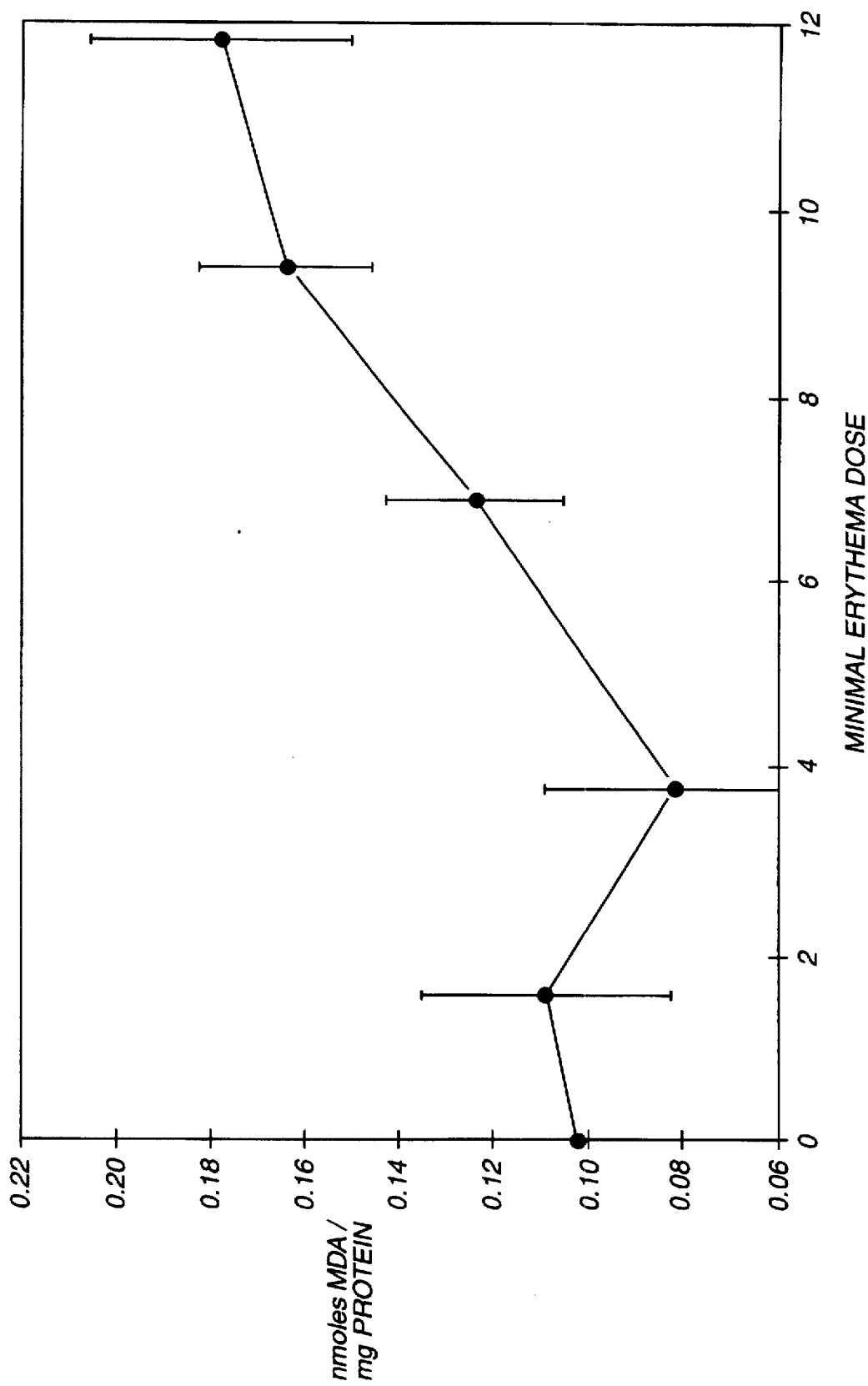
FIG. 11 shows the effect of exposure to Westinghouse FS40 Sunlamps on the production of lipid peroxidation in human dermal fibroblasts. Triplicate cultures were exposed to increasing number of MED.

Human dermal fibroblasts also demonstrate another chromophore in the UVB region of the spectrum. This effect may be produced by the small peaks in the dose distribution of the lamp which correspond with 297 and 303 nm shown best in FIG. 9. This effect of UVB on the production of lipid peroxidation in human dermal fibroblasts is further shown by the use of the Westinghouse FS40 Sunlamps (See FIG. 10) for dose distribution produced with this lamp alone). Using the UVB dominant FS40 Sunlamps, lipid peroxidation can still be induced in human dermal fibroblasts in a dose dependent manner as shown in FIG. 11.

Example 3
Cell type dependence for the production of lipid peroxidation

To determine whether or not there were variations in the response of different cell types to UVA, various normal and transformed cell types were examined for sensitivity to UVA-mediated lipid peroxidation (FIG. 12) as described above. Although all cell types examined in these experiments produced more lipid peroxidation in response to increased amounts of UVA, some cell-type differences in response were noted.

Normal human dermal fibroblasts and the mouse fibroblast cell lines Swiss 3T3 and J2-3T3 produced very different amounts of lipid peroxidation although the culture conditions were identical for these three cell types. Specifically, human dermal fibroblasts were about three times as responsive as Swiss 3T3 cells which were about three times as responsive as J2-3T3 cells. This increased response of dermal fibroblasts versus Swiss 3T3 cells may be due to the presence of the UVB sensitive chromophore identified in FIG. 8.

Similarly, normal human epidermal keratinocytes were much more responsive than the squamous cell carcinoma cell line (SCC 12B2) under similar culture conditions. Human epidermal keratinocytes (HEK) were the most responsive cell type when compared against the others using protein concentration as the internal control. HEK's produced the highest levels of lipid peroxidation per plate (greater than 10 nmoles per plate) compared to the other cell types tested. (This can be calculated by using the amount of protein per plate for each cell type which is given in the legend to FIG. 12.) Interestingly, they were also the only cell type to reach a maximal response in these experiments. This leveling of the effect of UVA on the production of lipid peroxidation in HEK's is not due to insufficient assay reagents since dilutions of these cell extracts produced the same levels of lipid peroxidation. Human epidermal melanocytes produced very low levels of lipid peroxidation when exposed to UVA under the culture conditions used.

Figure 13A:
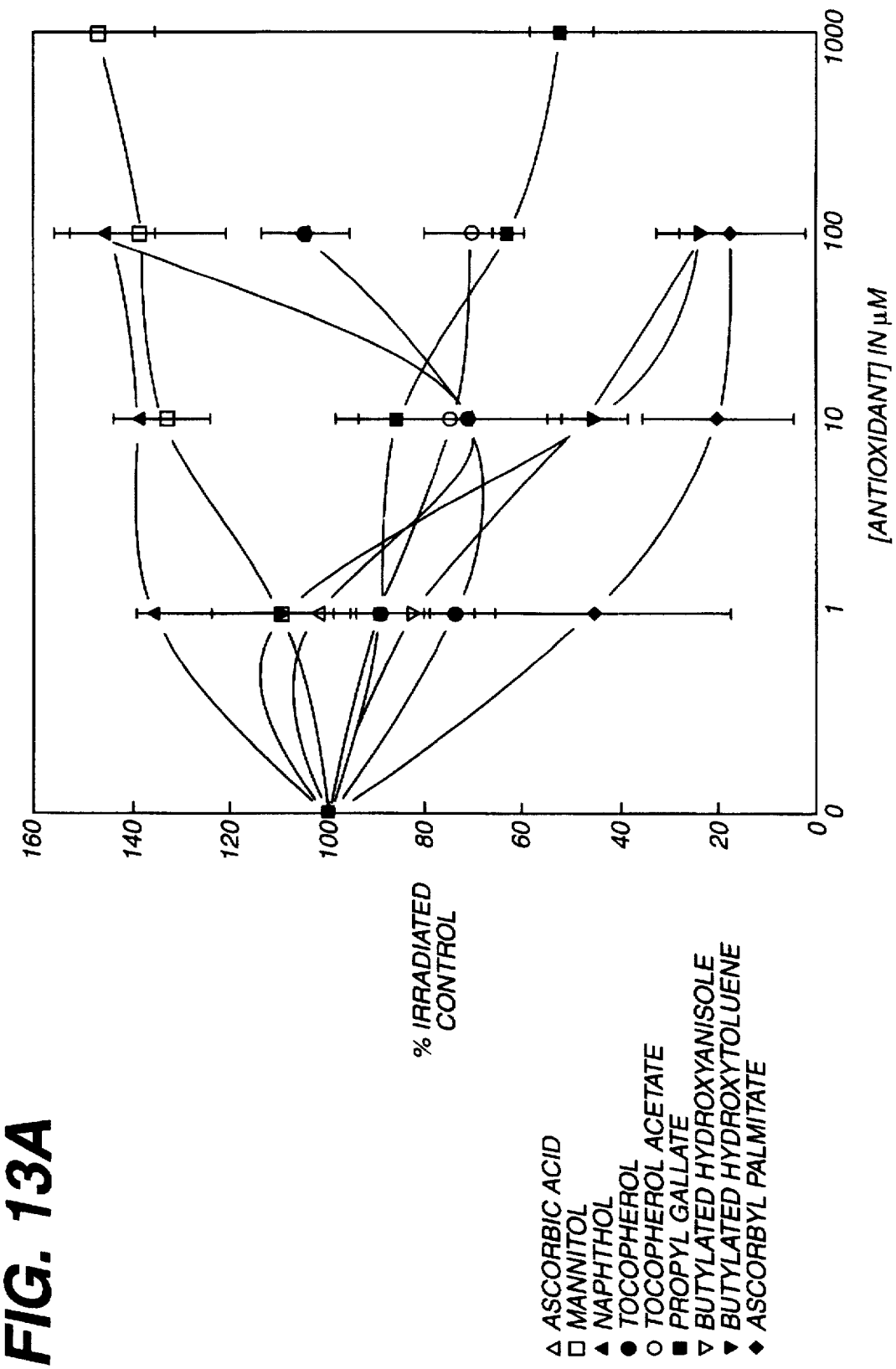
FIG. 13 shows the effect of antioxidants on UVA-induced lipid peroxidation. Triplicate cultures of Swiss 3T3 cells (A) and human dermal fibroblasts (B) were exposed to 60 joules/$cm^2$ UVA using Sylvania F40 350BL lamps in the presence or absence of various concentrations of antioxidants as shown.
Figure 13B:
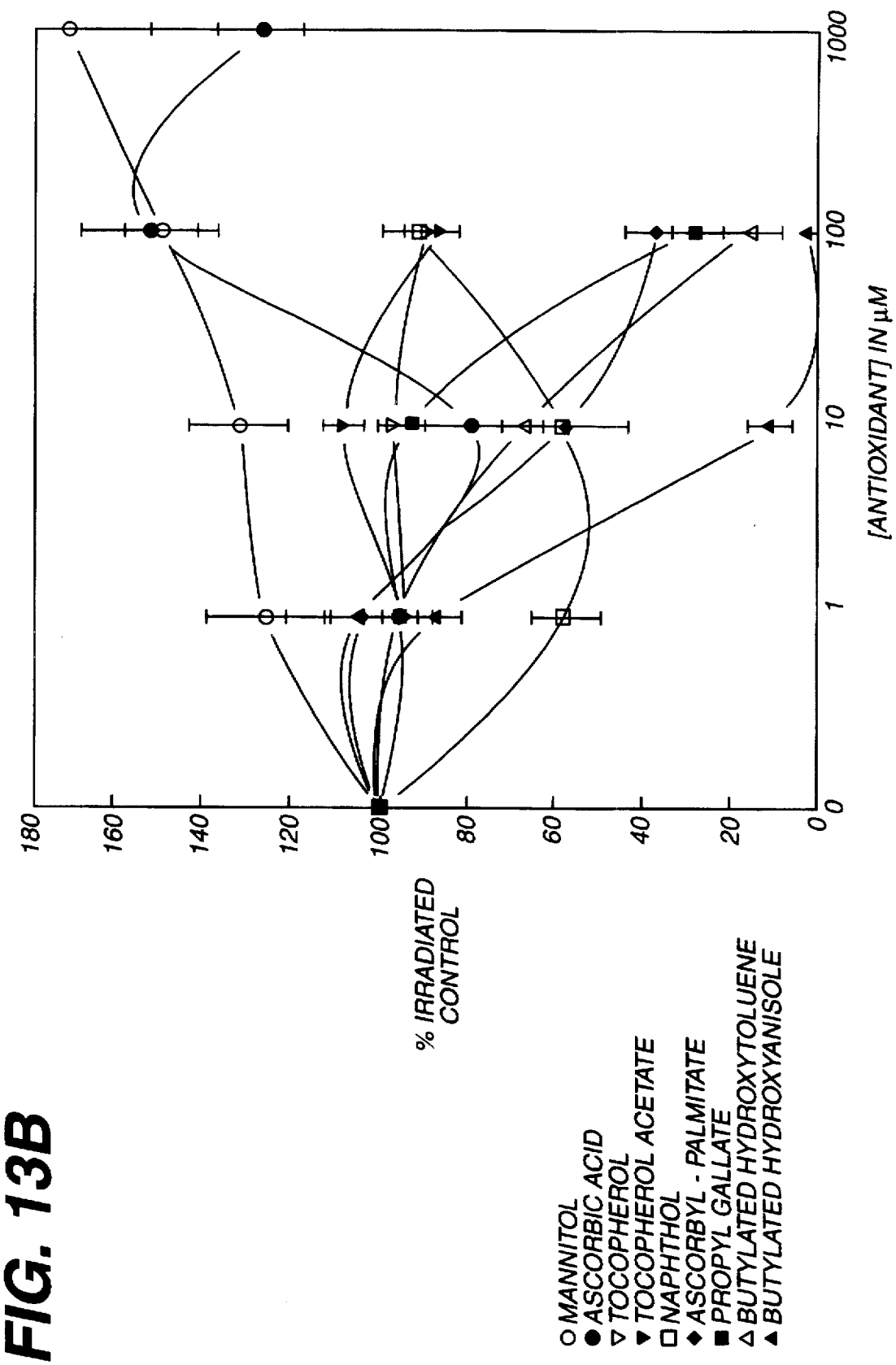

Example 4
Effect of antioxidants and oxygen radical scavengers on UV-induced lipid peroxidation The effect of various antioxidants on UVA-induced lipid peroxidation was also determined for both Swiss 3T3 cells and human dermal fibroblasts. The results are shown in FIG. 13. Confluent cultures were washed 2 times with 10 ml Hanks' Balanced Salt Solution (HBSS) before the addition of the treatment solution (2 ml per 100 mm culture dish and 1 ml per 60 mm culture dish) containing the indicated test agent in HBSS. Some materials were not soluble in water and were compared against controls containing 1% of the solvents. Culture dishes were irradiated through their lids and a lipid peroxidation assay was carried out as described above.

In these experiments, hydrophilic antioxidants, such as ascorbic acid and mannitol, were not only ineffective in preventing the UVA-induced production of lipid peroxidation, but they were detrimental in that levels of lipid peroxidation were actually increased 50–60% compared to irradiated control cultures. Lipophilic antioxidants, particularly butylated hydroxyanisole (BHA), butylated hydroxytoluene (BHT), and ascorbyl palmitate were the most effective in preventing UVA-induced lipid peroxidation. Some molecules, such as tocopherol and naphthol, produced unusual results. These molecules seem to prevent the production of lipid peroxidation at low concentrations (10 µM or less) while reversing that effect at higher concentrations.

Figure 14:
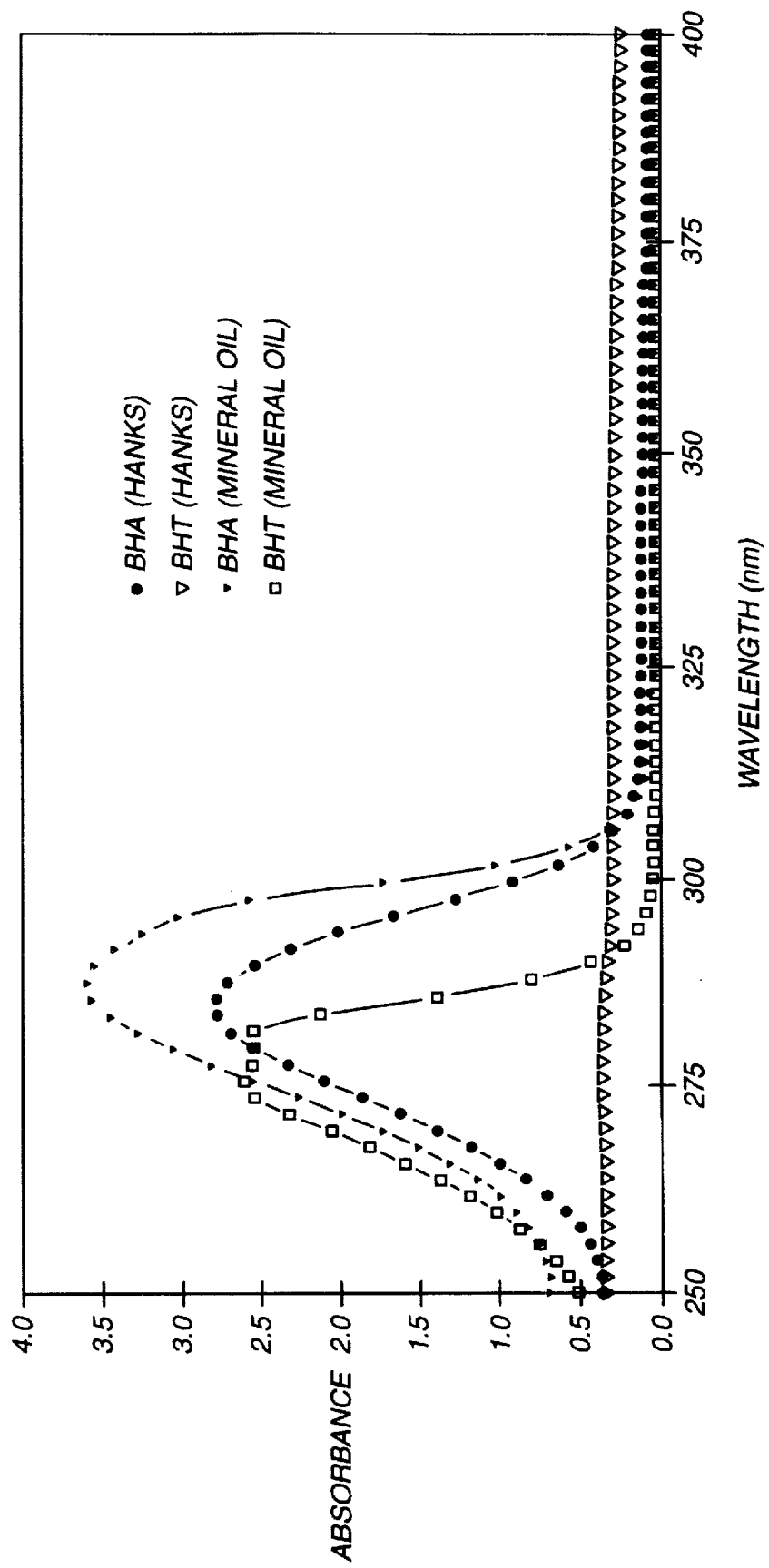
FIG. 14 shows absorbance spectra for BHA and BHT. Absorbance spectra were produced on 1 mM solutions in either Hanks Balanced Salt Solution or mineral oil using a Cary 2300 spectrophotometer.

To determine whether or not the absorbance characteristics of the antioxidants tested played a role in their ability to prevent UVA-induced lipid peroxidation, the UV spectra were produced for the antioxidants used in FIG. 13. The spectra for BHA and BHT are shown in FIG. 14. Interestingly, the absorbance for BHT was found to be extremely sensitive to the solvent used. If BHT was dissolved in aqueous Hanks Balanced Salt Solution. little absorbance was noted at the wavelengths studied. However, a large increase in absorbance was seen in samples dissolved in mineral oil. BHA was much less sensitive to differences in these two solvents. Neither BHA nor BHT absorb significantly in the regions covered by the spectral irradiance of the Sylvania F40 350BL lamps.

Figure 15:
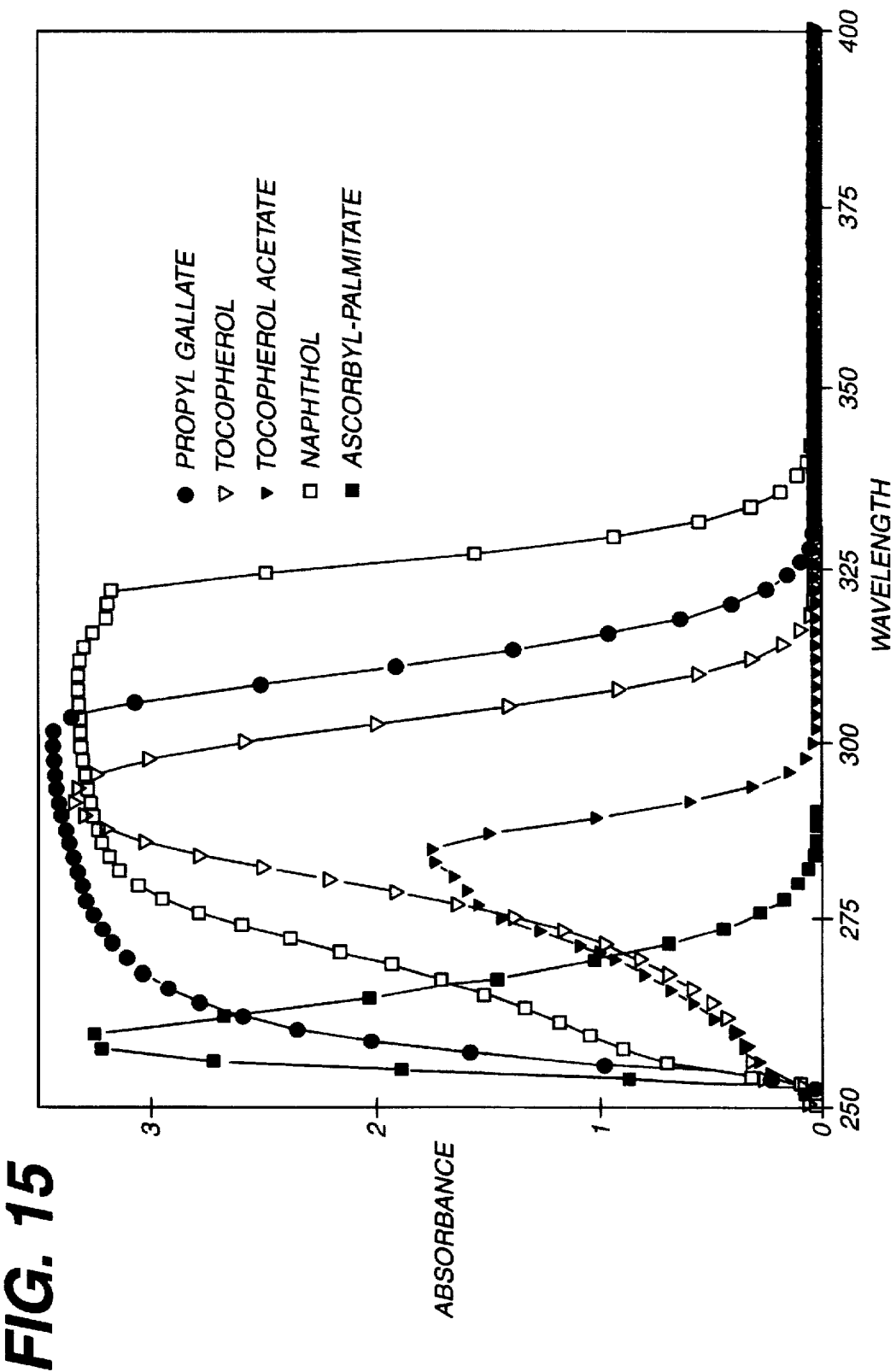
FIG. 15 shows absorbance spectra for selected lipophilic antioxidants. Absorbance spectra were produced on 1 mM solutions dissolved in dimethyl sulfoxide using a Cary 2300 spectrophotometer.

The absorbance spectra for the other antioxidants dissolved in dimethyl sulfoxide are shown in FIG. 15. α-Naphthol absorbs appreciably at wavelengths which overlap with the spectra produced by the Sylvania fluorescent lamps. (See FIG. 3 for comparison.) Tocopherol and propyl gallate absorb slightly in these overlapping regions while tocopherol acetate and ascorbyl-palmitate do not.

Figure 16:
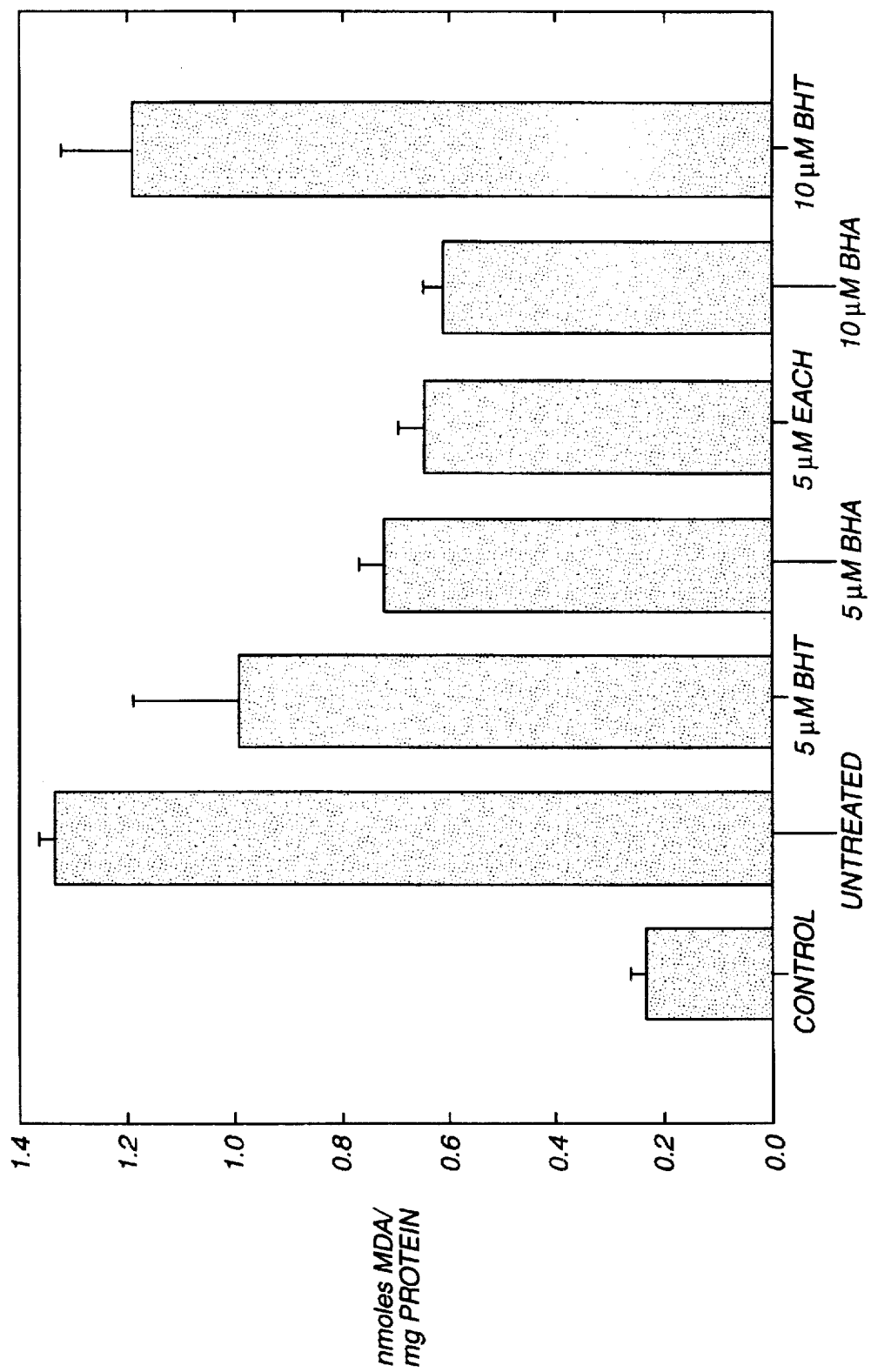
FIG. 16 shows the effect of a combination of BHA and BHT on UVA-induced lipid peroxidation. Triplicate cultures of human dermal fibroblasts were exposed to 60 joules/$cm^2$ UVA using Sylvania F40 350BL lamps in the presence or absence of various concentrations of BHA and BHT as indicated.

The ability of BHA and BHT to prevent UVA-induced lipid peroxidation was further examined by use of combinations of the two agents as shown in FIG. 16. The combination of the two agents did not show improvement over use of twice as much BHA alone. BHA was found to be more effective than BHT in these experiments.

Figure 17A:
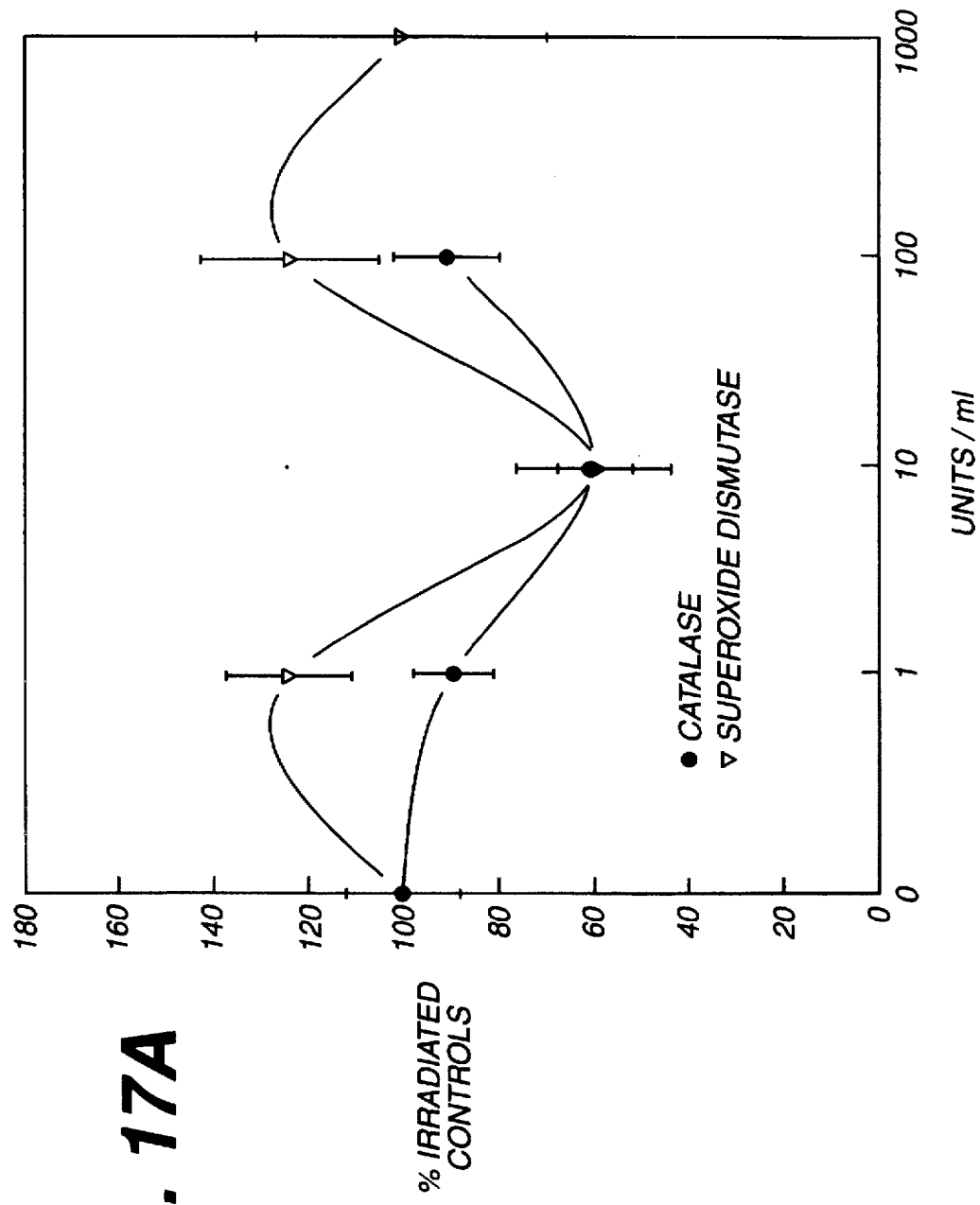
FIG. 17 shows the effect of oxygen radical scavenging enzymes on UVA-induced lipid peroxidation. Triplicate cultures of Swiss 3T3 cells (A) or human dermal fibroblasts (B) were exposed to 60 joules/$cm^2$ UVA using Sylvania F40 350BL lamps in the presence or absence of various concentrations of the indicated enzymes.
Figure 17B:
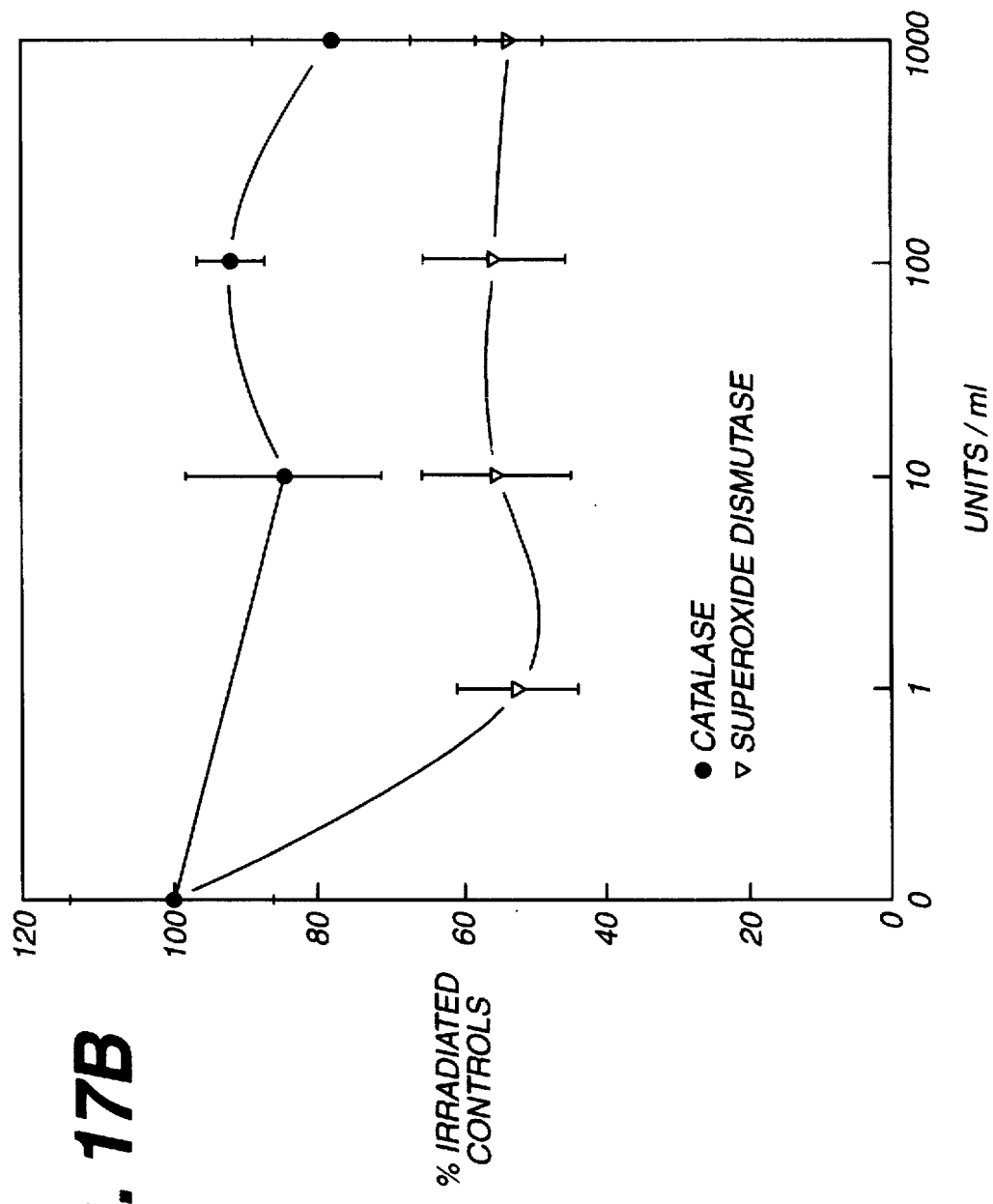

The potential use of oxygen radical scavenging enzymes as inhibitors of UVA-induced lipid peroxidation was also evaluated in both Swiss 3T3 cells (A) and human dermal fibroblasts (B) as shown in FIG. 17. No consistent effect was seen with either of these enzymes in Swiss 3T3 cells under the conditions tested (FIG. 17A). Interestingly, superoxide dismutase prevented about 45% of the induction of lipid peroxidation produced by UVA in human skin fibroblasts even at the lowest concentration of enzyme used (1 unit/ml) (FIG. 17B) with no additional effect with higher doses. Catalase had no effect in human skin fibroblasts (FIG. 17B).

Figure 18A:
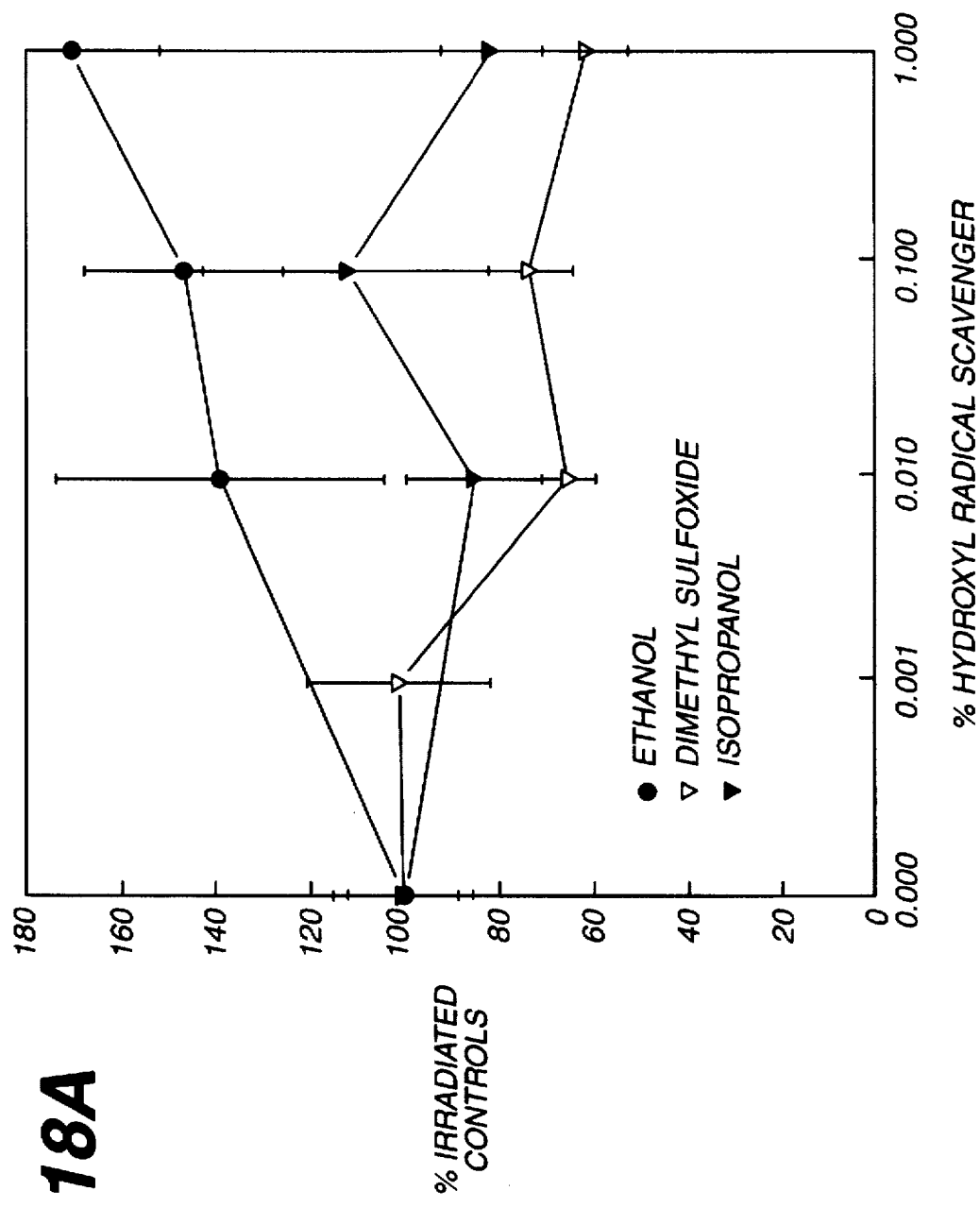
FIG. 18 shows the effect of hydroxyl radical scavengers on UVA-induced lipid peroxidation. Triplicate cultures of Swiss 3T3 cells (A) or human dermal fibroblasts (B) were exposed to 60 joules/$cm^2$ UVA using Sylvania F40 350BL lamps in the presence or absence of various concentrations of the indicated hydroxyl radical scavengers.
Figure 18B:
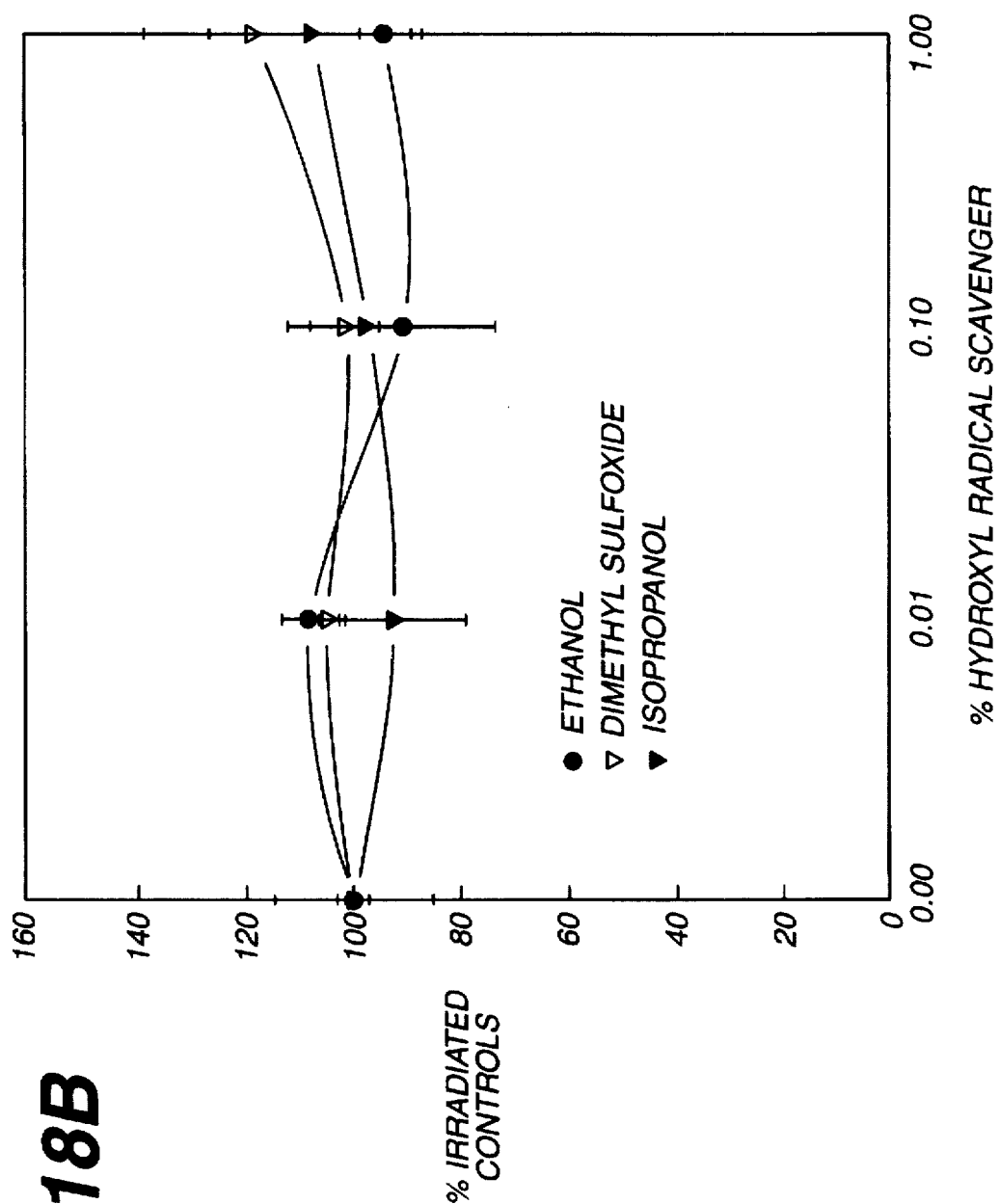

A number of alcohols and dimethyl sulfoxide are reported to have activity as hydroxyl radical scavengers [Gutteridge, J M C, *Biochem J* (1984) 224:697–701; Gutteridge J M C, "Lipid peroxidation: some problems and concepts." In: *Oxygen Radicals in Tissue Injury; Proceedings of a Brook Lodge Symposium.* 1988. B Halliwell, ed. Upjohn Co.: Augusta, Mich., pp. 9–19]. These molecules were, therefore, tested for their ability to interfere with UVA-induced production of lipid peroxidation as shown in FIG. 18. Ethanol somewhat stimulated the production of lipid peroxidation in Swiss 3T3 cells while it had no effect in human dermal fibroblasts. Dimethyl sulfoxide was mildly effective at inhibiting lipid peroxidation in Swiss 3T3 cells with no apparent effect in human dermal fibroblasts. Isopropanol had no effect in either cell type.

Example 5
The role of iron in UVA-induced lipid peroxidation

Figure 19A:
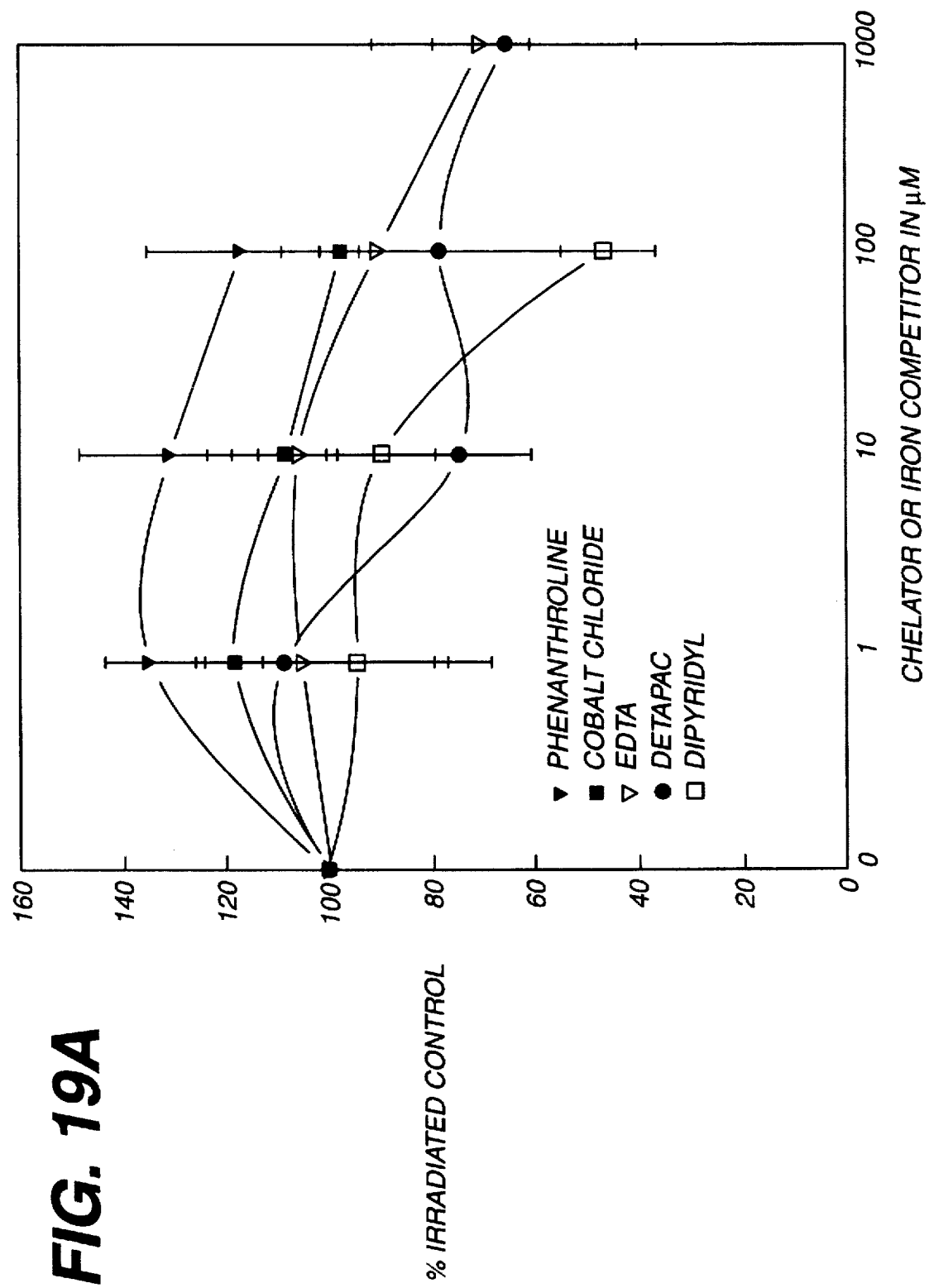
FIG. 19 shows the effect of chelators and iron competitors on UVA-induced lipid peroxidation in Swiss 3T3 cells (A) and human dermal fiborblasts (B). Triplicate cultures of Swiss 3T3 cells were exposed to 60 joules/$CM^2$ UVA using Sylvania F40 350BL lamps in the presence or absence of various concentrations of the indicated agents.
Figure 19B:
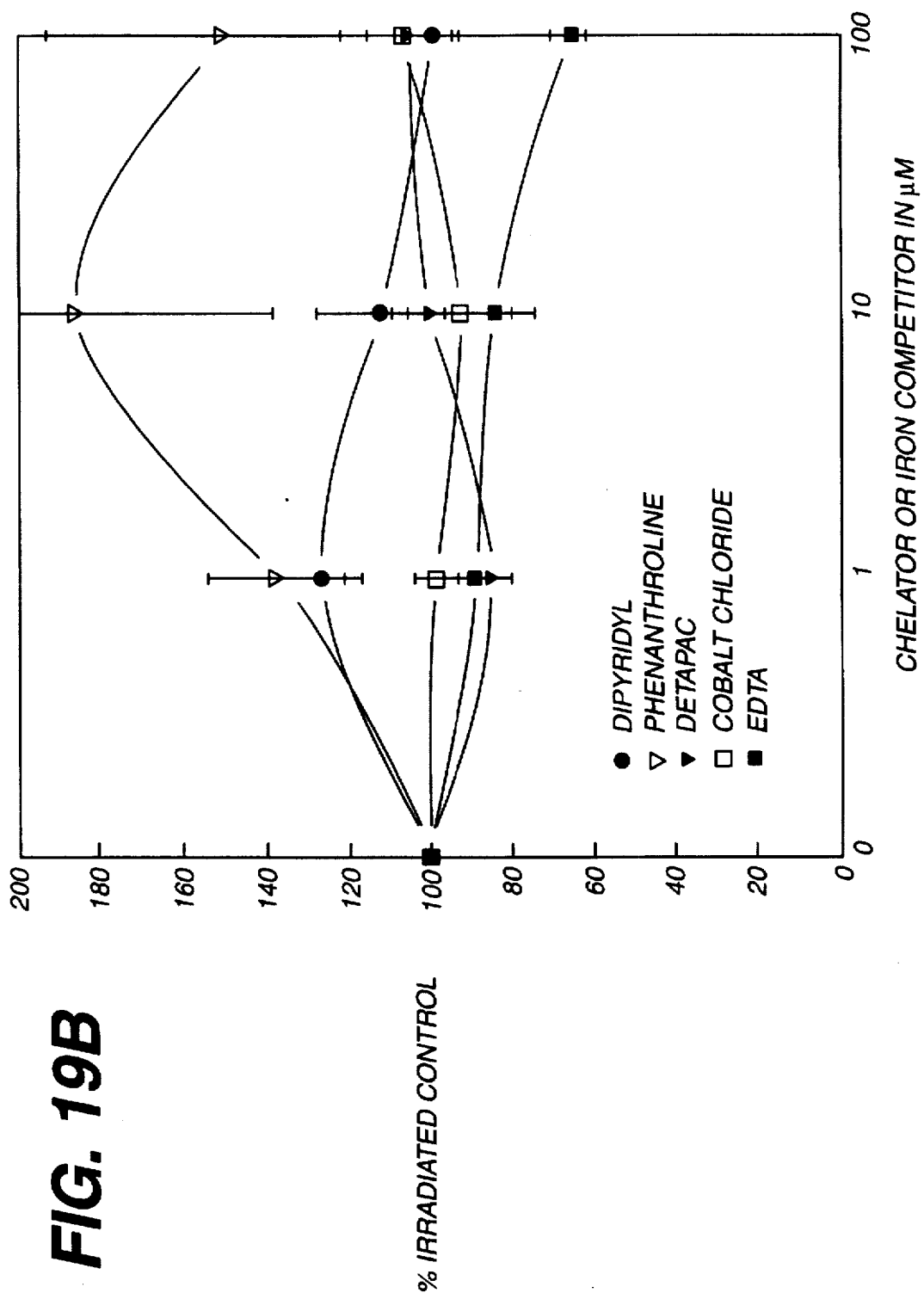

The potential role of iron, supplied either by the calf serum or media used to grow the cells, in the increase in lipid peroxidation due to UVA exposure was studied in Swiss cells and human dermal fibroblasts. The results are shown in FIG. 19. Confluent cultures grown in iron supplemented calf serum were washed 2 times with 10 ml HBSS then the chelator or iron competitor was added to the culture dish. The culture dishes were irradiated through their lids using a Sylvania F40 350BL lamp (60 joules/cm$^2$ UVA).

The results show that a variety of molecules that are either iron chelators or compete with iron in the production of lipid peroxidation was not effective in preventing UVA-induced lipid peroxidation in cultures fed with iron supplemented calf serum. In particular, the iron chelators phenanthroline, EDTA, DETAPAC and dipyridyl were mildly effective or ineffective in preventing UVA-induced lipid peroxidation in either Swiss 3T3 cells or human dermal fibroblasts. The iron competitor, cobalt chloride, was also ineffective in these experiments.

Figure 20:
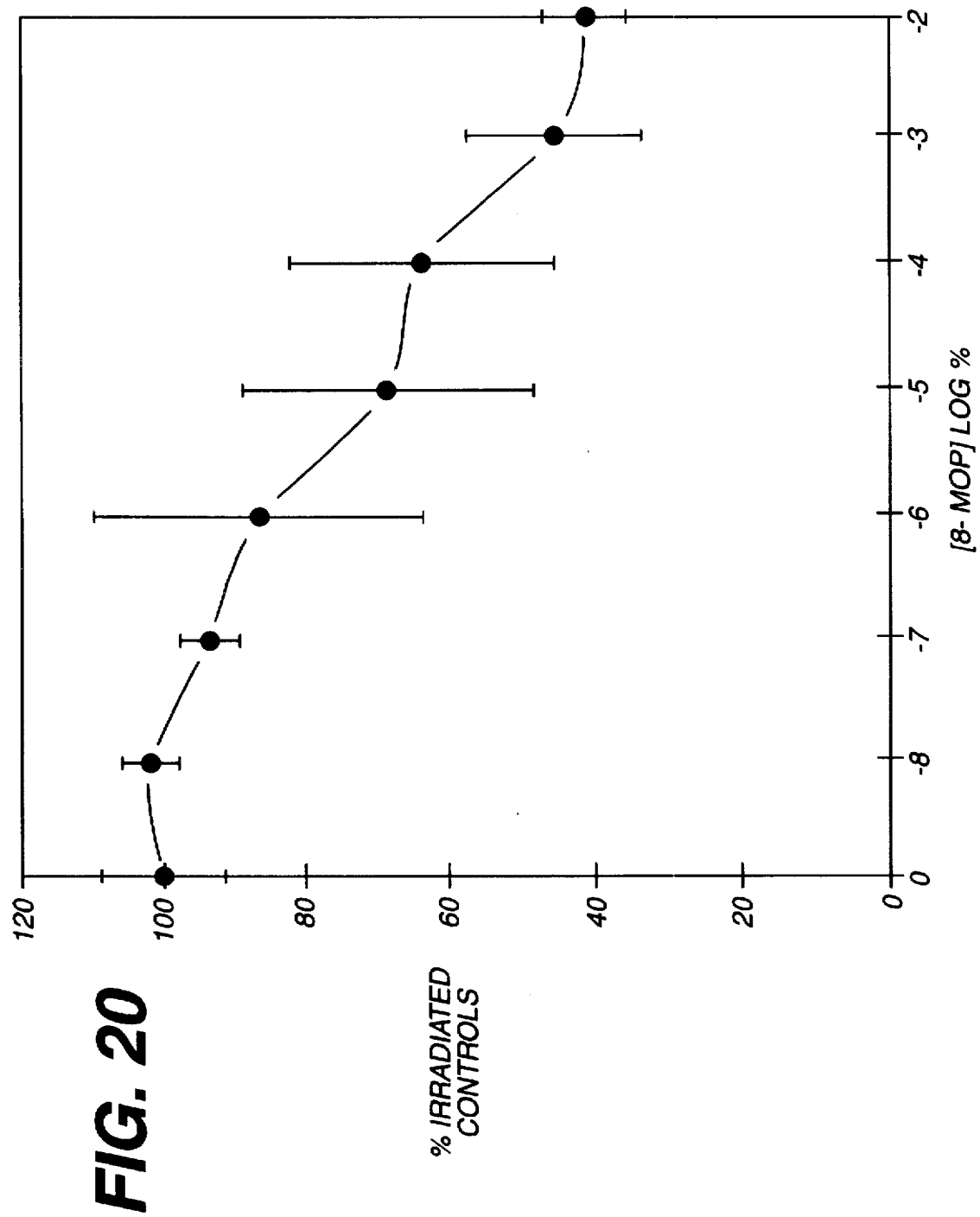
FIG. 20 shows the effect of 8-methoxypsoralen on UVA-induced lipid peroxidation. Triplicate cultures of Swiss 3T3 cells were exposed to 60 joules/$cm^2$ UVA using Sylvania F40 350BL fluorescent lamps in the presence of the indicated concentrations of 8-methoxypsoralen.

The ability of 8-methoxypsoralen (8-MOP) to stimulate the production of UVA-induced lipid peroxidation was also tested. As shown in FIG. 20, 8-MOP did not stimulate the effect of UVA in these experiments.

In summary, a number of types of molecules was found to be ineffective at preventing UVA-induced lipid peroxidation in the above experiments. These include hydrophilic antioxidants (FIG. 13), hydroxyl radical scavengers (FIG. 18), oxygen radical scavenging enzymes (FIG. 17) and iron chelators (FIG. 19). 8-Methoxypsoralen did not stimulate UVA-induced lipid peroxidation in this assay, indicating that its ability to act as a UVA-photosensitizer does not involve UVA-dependent production of lipid peroxidation (FIG. 20). Ascorbic acid has been shown to induce lipid peroxidation in an iron-dependent manner[Minotti G, *Chem Res Toxicol* (1993) 6:134–146; Bissett et al., *Photochem Photobiol* (1991) 54:215–223; Puppo et al., *Biochem J* (1988) 249:185–190; O'Connell et al., *Biochem J* (1985) 229:135–139; Miller et al., *Arch Biochem Biophys* (1993) 301:1–7; Geesin et al., *Arch Biochem Biophys* (1990) 278:350–355; Miller et al., *Arch Biochem Biophys* (1989) 271:113–119; Beach et al., *Arch Biochem Biophys* (1992) 297:258–264; Wefers et al., *Eur J Biochem* (1988) 174:353–357; Aruoma et al., *Biochem J* (1989) 258:617–620; Braughler et al., *J Biol Chem* (1986) 261:10282–10289; Minotti et al., *Lipids* (1992) 27:219–226; Ryan et al., *Crit Rev Toxicol* (1992) 22:119–141; Xu et al., *Inorg Chem* (1990) 29:4180–4184; Geesin et al., *Arch Biochem Biophys* (1991) 290:127–132], but no effect of iron, indicating its presence in these experiments, was detected.

Although hydroxyl radicals are thought to play a role in the production of lipid peroxidation, hydroxyl radical scavengers are generally poor at preventing lipid peroxidation [Gutteridge, J M C, *Biochem J* (1984) 224:697–701; Gutteridge J M C, "Lipid peroxidation: some problems and concepts." In: *Oxygen Radicals in Tissue Injury; Proceedings of a Brook Lodge Symposium.* 1988. B Halliwell, ed. Upjohn Co.: Augusta, Michigan, pp. 9–19; Geesin et al., *Arch Biochem Biophys* (1991) 290:127–132]. The inability of chelators to prevent UVA-induced lipid peroxidation suggests that these ions do not play a role in this in vitro phenomenon. However, free iron has been shown to participate in the UV-dependent production of lipid peroxidation in vitro[Van der Zee et al., *Free Radical Biol Med* (1993) 14:105–113], the development of photoaging in vivo[Bissett et al., *Photochem Photobiol* (1991) 54:215–223], and iron chelators are effective in preventing the characteristic changes involved in photoaging in mice[Bissett et al., *Photochem Photobiol* (1991) 54:215–223].

Superoxide dismutase has been reported to prevent sunburn cell formation in mice exposed to UVB[Danno et al., *J Invest Dermatol* (1984) 83:166–168], however it has been shown to be ineffective in preventing in vitro effects of UVA[Bose et al., *Radiat Res* (1993) 133:340–344] or in preventing lipid peroxidation induced by a variety of means [Gutteridge J M C, "Lipid peroxidation: some problems and concepts." In: *Oxygen Radicals in Tissue Injury; Proceedings of a Brook Lodge Symposium.* 1988. B Halliwell, ed. Upjohn Co.: Augusta, Mich., pp. 9–19; Miller et al., *Arch Biochem Biophys* (1989) 271:113–119; Geesin et al., *Arch Biochem Biophys* (1991) 290:127–132; Bucher et al., *Biochem Biophys Res Commun* (1983) 111:777–784]. This lack of activity for superoxide dismutase probably results from its inability to partition into lipid bilayers where the oxygen radicals are formed. * * * * * * *

The foregoing invention has been described in some detail for purposes of clarity and understanding. It will also be obvious that various combinations in form and detail can be made without departing from the scope of the invention.

All publications mentioned hereinabove are hereby incorporated by reference.

What is claimed is:

1. A method of protecting mammalian skin from oxidative effects of ultraviolet A radiation comprising topically applying to the skin an effective amount of a photoprotective composition, said compositive comprising a lipophilic antioxidant that does not have appreciable absorbance near wavelengths of 320–380 nm.

2. The method of claim 1 wherein said lipophilic antioxidant does not have appreciable absorbance near wavelengths of 345 nm.

3. The method of claim 1 wherein said composition comprises from about 0.0001% to about 10% (w/w) of said lipophilic antioxidant.

4. The method of claim 3 wherein said composition comprises from about 0.01% to about 1% (w/w) of said lipophilic antioxidant.

5. The method of claim 4 wherein said composition comprises from about 0.1% to about 0.5% (w/w) of said lipophilic antioxidant.

6. The method of claim 1 wherein said lipophilic antioxidant is selected from the group consisting of butylated hydroxyanisole (BHA), butylated hydroxytoluene (BHT) and ascorbyl-6-palmitate.

7. The method of claim 1 wherein said composition is in a solid, liquid or aerosol form.

8. The method of claim 7 wherein said composition is formulated into a liposomal formulation, an emollient, a liquid, a cream, a gel, an ointment, a microemulsion, or a solution.

9. The method of claim 1 wherein said photoprotective composition further comprises a sunblock agent or a sunscreen agent.

10. The method of claim 9 wherein said sunblock agent is selected from the group consisting of zinc oxide and titanium dioxide.

11. The method of claim 9 wherein said sunscreen agent is selected from the group consisting of p-aminobenzoic acid and its derivatives, anthranilates, salicylates, cinnamates and their derivatives, naphtholsulfonates, benzophenones, dibenzoylmethane derivatives, and tannic acid and its derivatives.

* * * * *